United States Patent [19]

King et al.

[11] 4,156,430
[45] May 29, 1979

[54] INSTRUMENTATION FOR PACEMAKER DIAGNOSTIC ANALYSIS

[75] Inventors: Eugene King, Yardley, Pa.; Paul S. Chudoba, Mt. Holly; Howard M. Hochberg, East Windsor, both of N.J.

[73] Assignee: Hoffmann-La Roche Inc., Nutley, N.J.

[21] Appl. No.: 842,659

[22] Filed: Oct. 17, 1977

Related U.S. Application Data

[63] Continuation of Ser. No. 620,545, Oct. 8, 1975, abandoned.

[51] Int. Cl.² .............................................. A61N 1/30
[52] U.S. Cl. ............................................... 128/419 PT
[58] Field of Search .................. 128/2.05 R, 2.06 A, 128/2.06 B, 2.06 F, 2.06 R, 2.1 A, 419 PT; 340/347 DD

[56] References Cited

U.S. PATENT DOCUMENTS

| | | | |
|---|---|---|---|
| 3,123,768 | 3/1964 | Burch et al. | 128/2.06 R |
| 3,587,087 | 6/1971 | King | 340/347 DD |
| 3,721,230 | 3/1973 | Ziernicki | 128/2.06 B |
| 3,871,363 | 3/1975 | Day | 128/419 PT |
| 3,885,552 | 5/1975 | Burdick et al. | 128/419 PT |
| 3,897,774 | 8/1975 | Kennedy | 128/419 PT |
| 3,910,257 | 10/1975 | Fletcher et al. | 128/2.1 A |
| 3,946,744 | 3/1976 | Auerbach | 28/419 PT |

OTHER PUBLICATIONS

Thomas et al., "Medical and Biological Engineering", vol. 9, No. 5, Sep. 1971, pp. 503–509.

Mancini et al., "IEEE Transactions on Biomedical Engineering," vol. BME. 22, No. 4, Jul. 1975, pp. 281–286.

*Primary Examiner*—William E. Kamm
*Attorney, Agent, or Firm*—Jon S. Saxe; Bernard S. Leon; Mark L. Hopkins

[57] ABSTRACT

Apparatus for diagnostic analysis of patient-installed pacemaker devices. Patient connection is made via standard ECG leads and an electrically floating front end subassembly having means providing precise gain to the paced ECG input signal and conversion thereof to a digital form via very high rate, monobit delta-sigma modulation digitization. The front end also contains special overload indication circuitry, a reciprocal attenuation network to ensure high fidelity of the information being processed by the system and crystal clock controlled calibration means for providing a validity check of virtually the entire system. A pacer pulse sensing network provides as separate outputs in analog form the on-line, real-time, paced ECG and the individual pulses generated by the pacemaker device. A memory/magnification subassembly is also included, operating on the digitized paced ECG information, calibration and clock outputs from the front end, as well as the identified pacer pulses from the pacer pulse sensing network, to selectively provide as outputs, magnified X1000 in time, the calibration waveform and the pacemaker-generated pacer pulses in either digital or analog form. These and the on-line, real-time paced ECG signal are available for recordation locally and for transmission over the telephone.

26 Claims, 16 Drawing Figures

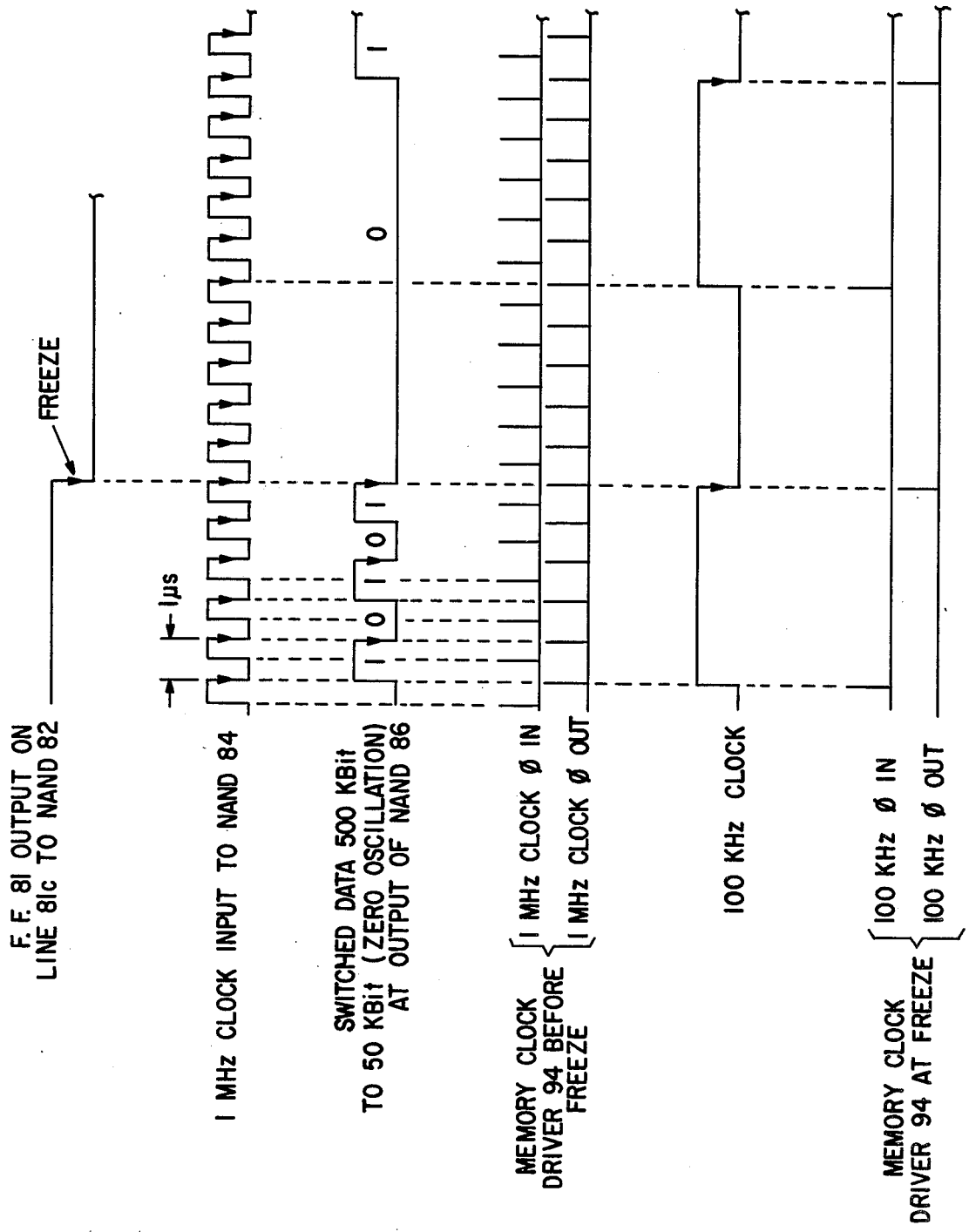

INSTRUMENTATION FOR PACEMAKER DIAGNOSTIC ANALYSIS

This is a continuation, of application Ser. No. 620,545 filed Oct. 8, 1975, now abandoned.

BACKGROUND OF THE INVENTION

This invention relates to instrumentation designed to simplify the very important and useful but relatively complex procedure of in vivo electronic examination of pacemakers (pacers).

The usefulness of this electronic examination has been well documented in the literature. Electronic cardiac pacemakers have a finite but not totally predictable lifespan. Paced patients require routine checkups to determine if the pacer is operating correctly, if the catheter leads are correct, and if the battery is running down. Routine evaluation of the pacer is prudent because it allows more accurate prediction of failure and thus may prevent wasteful early replacement as well as dangerous failure, i.e. frequent routine checks of pacemaker function are useful to optimize pacemaker longevity by allowing replacement only when necessary.

Impending failure may be heralded by slowing of the intrinsic pacer rate, change in pacer waveform duration, amplitude or shape. Failure to function correctly (inhibit, trigger) may be elicited by proper tests. Presently, complete checkups require visiting an electronic "checkup" center. That is paced patients are "followed" by specialized centers which use electronic equipment to test for pacer function, catheter integrity and battery life. Checkups occur at more frequent intervals as the pacer wears, until they may be monthly in the second or third year. The clinic visits are required because heretofore only such facilities have the assembly of equipments needed to completely test the pacer.

Electronic checks for pacer function integrity and remaining lifespan usually include recording of EKG rhythm strips to determine paced rhythm (with magnet) and spontaneous rhythm (without magnet), accurate electronic measure of pacer rate (or impulse interval), accurate electronic measure of pace (waveform) widths, and frequently a photograph (for inspection and measurement) of a high-speed oscillographic representation of the (expanded) pacer waveform.

This valuable electronic exam heretofore has required an assembly of assorted complex scientific instruments and technical equipments which should only be operated by special and experienced technicians or nurses, which assembly is large, difficult to operate, expensive to use, time consuming and are all not safely isolated, and which can require disrobing of the patient during examination. The photograph may add considerable time to the examination. The size of the equipment assembly alone requires that patients be brought to it rather then it being brought to the patient. The need to travel to the center for a checkup gives rise to a costly and burdensome task, with potential risk, for nursing home and home-bound or bedridden patients or patients living at great distances.

A typical prior art pacemaker clinic test setup is comprised of an oscilloscope with a differential input, a wide band amplifier plus a suitable "Polaroid" type camera for pacer waveform analysis, a special counter for interval and width measurement of highest accuracy and a cardiographic recorder for recording of the paced-and-spontaneous ECG. None of the above test equipments is safety isolated from ground. Photocopies of the photograph of the patient's pacer waveform are understandably of poor quality and may be blurred. As a practical matter, virtually none of the measured parameters is available and suitable for telephone transmission to, for example, a regional pacemaker clinic in case consultation is needed, or in the general situation of a remotely located patient unable for whatever reason to come to the pacemaker clinic.

As a partial or complimentary alternative to clinic checkups, there are presently available systems permitting the remote transmission of some of the required information to a clinic over the telephone, i.e. it may be considered as rather standard practice to transmit EKG and derive pacer spike interval. The usual telephone checkup consists of the patient placing a magnet over his pacer (to switch the pacer from the demand mode to the fixed rate mode), placing simple ECG leads on himself, and transmitting either his ECG and the impulse or the pacer impulse only via telephone. This is accomplished by changing the ECG into a frequency modulated tone and sending the tone into the telephone. At the center a technician uses a demodulator to reassemble the ECG and record it. An interval counter provides a more or less accurate measure of rate. The pacer waveform cannot be examined because the shape is completely lost during transmission. There is no known pacemaker follow-up telephone system that can measure and transmit the pacer pulse waveform and to provide hard copies thereof, i.e. high fidelity pictures etc. of the pacer pulse waveform in for example crystal precise time expansion of say X1000 or any other desired time base. Moreover, there is presently available no telephone arrangement capable of providing transmission of the pacer waveform, in particular for measurement and analysis of the decay time of the slope of the trailing edge of the waveform, which relates to current drain, and, therefore, battery life.

As part of an overall consideration of the shortcomings and drawbacks of the prior art, it would be highly desirable to provide an arrangement which would allow any group caring for paced patients to provide the best possible data for pacer life optimization, and such is a principle object of this invention.

It is, moreover, highly desirable to provide a portable, telephone type system capable of acquiring and transmitting from and to almost anywhere all the information usually acquired only at the checkup (i.e. on-line, real-time ECG, expanded calibration and expanded pacer waveform) of the patient at a center, by telephone for remote analysis, and such is another principle object of this invention.

It is a further object of this invention to provide instrumentation which improves the quality of care of paced patients and so simplifies the examination procedures as to make this quality care available more economically and to far greater numbers of patients, as well as enabling any EKG technican to obtain the most complete results.

It is another object of this invention to provide instrumentation which is fully capable of performing, at least, all of the measurements above-mentioned in connection with the prior art and which produces a thousand-fold time-expanded pacer waveform on an EKG recorder, all with full safety isolation.

It is yet a further object to provide a system capable of sensing, extracting, measuring, magnifying and reproducing with extreme accuracy all vital parameters of a pacemaker pulse through standard ECG leads of a patient with implanted or external transvenous pacemakers of all kinds.

SUMMARY OF THE INVENTION

According to the broader aspects of this invention there is provided a system for evaluating an artificial pacemaker operatively connected to a paced patient comprising electrically floating first means for converting an input signal containing artificially paced heart function information derived from the patient to a digital representation thereof of predetermined form and high rate, and second means for selectively deriving from said digital representation an exact analog reproduction of at least one artificially generated pacer pulse present in said input signal, said analog reproduction being magnified in time by a predetermined amount.

Moreover, there is provided in a system for providing transtelephonic information derived from a patient remotely located from an information processing center, in which the information to be transmitted to the center is related to heart function and includes pacemaker device-generated pacer pulse information, the combination comprising: (a) electrically isolated first means local to the patient and responsive to the input of said information for providing a high rate, monobit digitization of said information; (b) second means responsive to said first means for selectively isolating from said digitized representation of said information that portion thereof pertaining to at least one pacemaker device-generated pacer pulse and for providing same in analog form of high fidelity relative to said patient-derived information and magnified a predetermined amount in time for transmission to the information processing center.

The instrumentation is comprised essentially of two major portions, the electronics and the recording means. The electronics portion allows selection of any of three standard limb leads (all analyses are performed from limb leads), and is comprised of a three-lead select ultrawideband floating safety-isolated EKG preamplifier with attenuation control and calibration injection. The EKG is digitized at a high rate. The pacer pulse is sensed and stored, and it is replayable at for example 1000X slower speed. A 1 KHz calibration squarewave is available to provide via a unique arrangement a "go/no 'go" check for the entire system, including the floating front end. Digital readout means are provided for pacer pulse width and interval in milliseconds and pacer rate in beats/minute. A strip chart printout is provided for on-line, real-time paced EKG, the magnified calibration waveform and the magnified pacer waveform. These facilities are provided at least in part by virtue of a unique memory freeze control technique and novel pulse width discrimination circuitry.

In contrast to the usual oscilloscopic set-ups, the EKG is fully isolated (i.e. < 5μ amp. leakage). The EKG is calibrated for both time and amplitude by a crystal controlled circuit. The system is portable, allowing it to be brought to nursing homes and to the homes of invalids, thus inter alia potentially avoiding cost while providing better care.

The following are automatically and immediately available for digital display in a system according to the invention: pacer rate to bpm (to ±0.15%), pacer interval in msec (to ±0.01 msec), pacer waveform width (to ±0.01 msec). The oscilloscopic photograph of the prior art is replaced by a write-out of an ordinary EKG strip chart. In fact, another unique feature of the instrumentation is its ability to display an expanded pacer waveform on an ordinary EKG strip chart. Because the waveform may vary within a range of 0.25 mv to one volt in amplitude at the patient's skin surface, an attenuation system is needed to ensure that the waveform fits on the chart. This is accomplished with a relatively simple overload adjustment approach, wherein the need for attenuation is indicated based on the presence of an alarm indicating signal overload, i.e. the waveform may be too large to fit on the paper. This assures time magnified waveform reproduction and non-ambiguous ease of operation by untrained hospital personnel. The strip chart automatically displays one or more waveforms, expanded 1000X in time, depending on wanted recorder (recirculation) running time.

Waveform expansion is accomplished by continuously sampling and storing the EKG, with the capability to select for printout a desired portion of the EKG. This invention offers inexpensive storage of short time periods of very high data rate.

The system employs a simplified one Megabit (1 Mbit), monobit, delta-sigma modulation digitization technique at its floating front end, in providing digital transmission through optical couplers (and also avoiding costly and current-consuming standard analog-to-digital converters). The high 1 Mbit digitization in turn allows trouble-free (noise-free, distortionless) transmission of wide bandwidth signals through its high sampling frequency of 1 MHz.

There is, moreover, provided a system employing a DC-to-50 KHz bandwidth along with a common mode rejection of greater than 80 db (to reduce the 60 Hz noise from electrical fields) and 40 megohm input impedance (to reduce the effects of differing resistances from the electrodes.

The invention further provides for a unique portable telephone system arrangement with transmission of stored and expanded calibration waveform, so that, for example, the receiver station can compensate for telephone line and exchange loss and thus obtain a calibrated reference waveform. It also allows for phone transmission of stored and expanded pacer pulse waveform (wide bandwidth due to narrow pulse with fast rise and fall times) with very high fidelity. Any standard graph recorder can reproduce the slowed, expanded pacer waveform at the transmitter and/or receiver side. The actual pacer waveform width (duration) can be measured digitally at the patient's (transmitting) side, and at the telephone receiving side the width can be measured very accurately from the expanded analog pacer waveform on the strip chart and/or through standard digital width counting techniques.

The pacer repetition rate (interval) can be measured at the patient's (transmitting) side with very high accuracy, and at the telephone receiving side through transmission of a wide pulse or pulse burst for every sensed pacer pulse.

BRIEF DESCRIPTION OF THE DRAWINGS

The above-mentioned and other objects and features of this invention will become more apparent by reference to the following description taken in conjunction with the accompanying drawings, in which:

FIGS. 6A and 6B are timing diagrams illustrating the operation of the circuitry in FIGS. 4 and 5;

DESCRIPTION OF THE PREFERRED EMBODIMENT(S)

Figure 1:
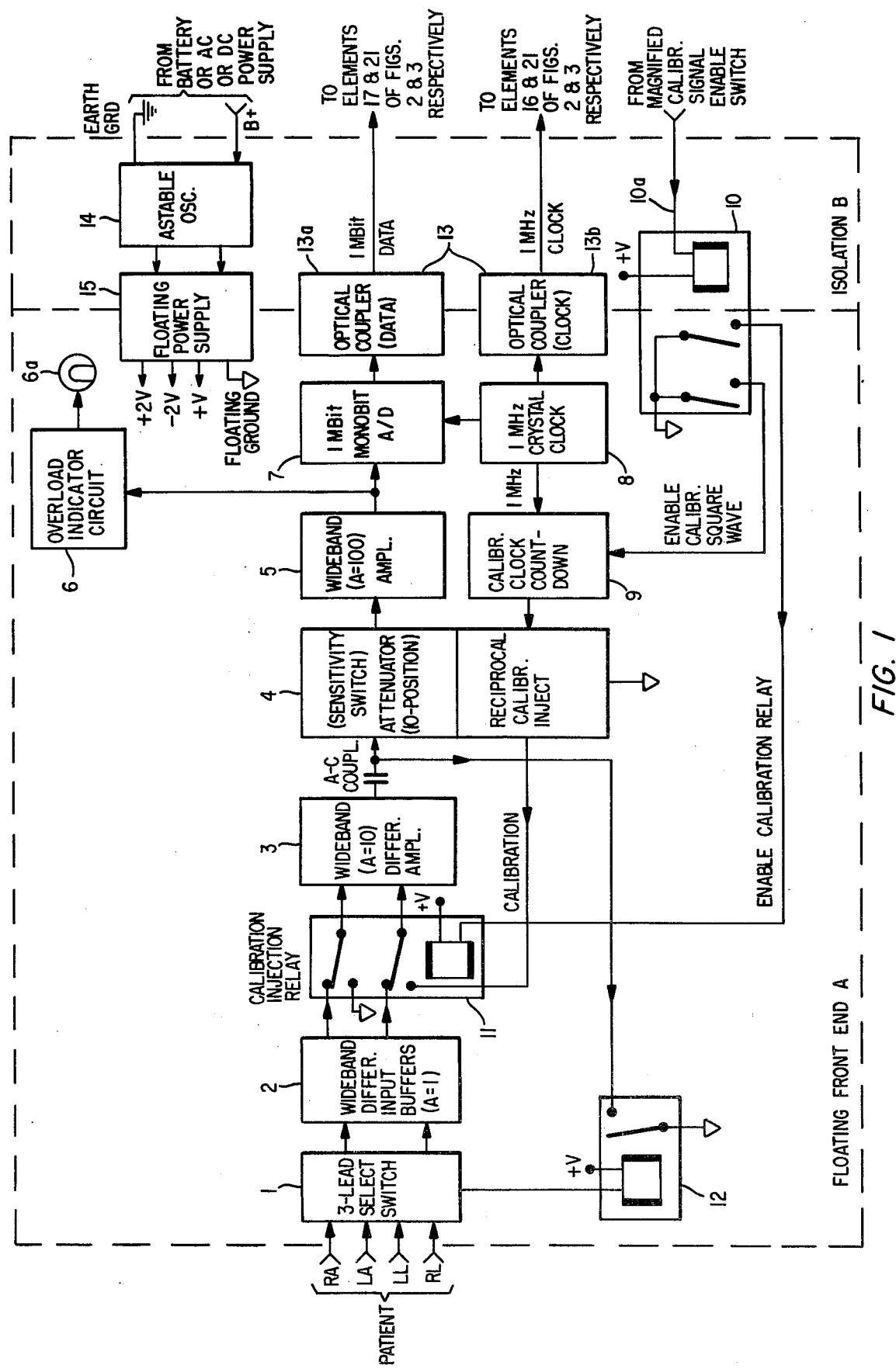
FIG. 1 is a block diagram of the floating front end of the system according to the invention, coupled to the paced patient and suitably electrically isolated from the rest of the system.

Regarding the preferred arrangement of system herein described, reference is made to the block diagram of FIG. 1 which illustrates the floating front end A of the system together with the isolation means portion B employed. A paced patient (not particularly shown) is associated with the pacemaker diagnostic analyzing apparatus via conventional EKG leads (RA, LA, LL, RL), which leads are terminated in a conventional three-lead selection switch 1 (RL [floating ground] may or may not be connected to the patient depending on signal-to-noise ratio). The three-lead switch 1 allows the standard three ECG leads, i.e. Lead I, Lead II and Lead III.

The selected signal from switch 1 is coupled to and treated by a floating wide band differential amplifier arrangement of constant gain, i.e. X1000 (60 db), capable of passing pacemaker pulses down to 20$\mu$ sec. width. This differential amplifier arrangement comprises stages 2, 3 and 5, i.e. two wideband X1 gain differential input buffer stages 2, wideband X10 gain differential amplifier stage 3, and wideband X100 gain amplifier 5, suitably coupled to calibration and attenuation circuitry.

More particularly, differential input buffer stage 2 is coupled to the output lines of lead select switch 1 on the one hand and to a calibration injection relay arrangement 11 on the other hand. The output leads of calibration inject relay 11 represent the input leads to the X10 gain differential amplifier stage 3, which in turn is AC coupled to a ten-position attenuation (sensitivity) switch/reciprocal calibration inject switch arrangement 4. The output of the ten-position attenuator switch is coupled to the X100 gain amplifier stage 5. The overall purpose of the ten-position attenuator network 4 is to assure high fidelity pacer waveform reproduction (leading and trailing edge, rise and fall times, plateau and decay) without clipping.

Lead switch 1 also has associated therewith a relay arrangement 12, which is intended to provide an AC-coupling shunt relay function to the floating ground, and which is activated by lead switch select stage 1 during lead switching in order to avoid hangup (saturation) of the amplifier arrangement (3,5) and possible overloading and/or malfunction of later stages.

Still with reference to the floating front-end A of the system according to the invention, the output of wide band amplifier stage 5 is fed to a simplified analog-to-digital converter 7 employing a one Megabit (i.e. 1 Mbit), monobit, delta-sigma modulation technique. The A/D stage 7 allows digital transmission through optical coupler 13a and also avoids the use of the costly and relatively high current-consuming conventional A/D converters. This latter point is highly significant in a battery type portable arrangement such as is contemplated herein. The high, 1-Mbit digitization in turn allows trouble-free (noise-free, distortionless) transmission of wide bandwidth signals through a high sampling frequency of B 1 MHz.

The 1 Mbit, monobit A/D converter stage 7 is governed by a 1 MHz crystal clock 8, which, like the output of A/D converter 7, is also coupled via an optical coupling arrangement 13b as an output from the floating front end A. Optical couplers 13, then, provide for the safety isolated transmission of the two digital signals comprising the floating monobit, 1 Mbit data and 1 MHz clock. The transmission of digital data and clock avoids the distortion and noise prone, as well as difficult, transmission of wideband analog signals.

The output of wideband amplifier stage 5 is also coupled to an overload circuit arrangement 6 which includes a light indicator 6a. The purpose of the overload indicator stage 6 is to inform the operator whenever the position of the attenuator switch 4 should be changed in order to avoid signal overloading, thus, assuring true magnified waveform reproduction as well as non-ambiguous ease of operation of this system by those of only limited professional training.

Also included in the floating front end A is an isolated relay arrangement 10 employed to exercise a calibration command in conjunction with calibration relay arrangement 11. By the arrangement according to the invention there is provided a true front-to-back calibration check, including virtually the entire floating front end A. Associated with the combined arrangements of relays 10, 11 is a conventional calibration clock countdown circuit, wherein the 1 MHz crystal clock output is converted to a 1 KHz squarewave signal. This, in turn, is fed through the reciprocal calibration injection portion of switch 4 and on to the two-position double-throw calibration inject relay arrangement 11, wherein, upon an actuation (enable calibration injection relay) signal being present from the relay arrangement 10, which is effected as a result of the actuation of relay arrangement 10 via a (pushbutton) magnified calibration signal enable switch (element 65 in FIG. 3), the 1 KHz squarewave calibration signal is passed through the system beginning with differential amplifier stage 3. Relay 10 also assures safety isolation between the floating and earth grounded portions of the system. The injection of 1 KHz crystal-derived calibration squarewave allows rapid and precise gain and time calibration from the floating first amplifier 3 throughout the entire memory-magnification-reproduction sequence of the system.

As part of the isolation (section B of FIG. 1) provided within the system herein described, power to the floating front end A is supplied via an earth-ground-referenced astable oscillator 14, coupled to a battery, or AC/DC power supply which in turn drives a floating power supply 15, thus isolating the patient front end A (i.e. stages 1 to 12), from a power standpoint, from the remainder of the system. The floating power supply provides a number of positive and negative potentials referenced to a floating ground.

Figure 2:
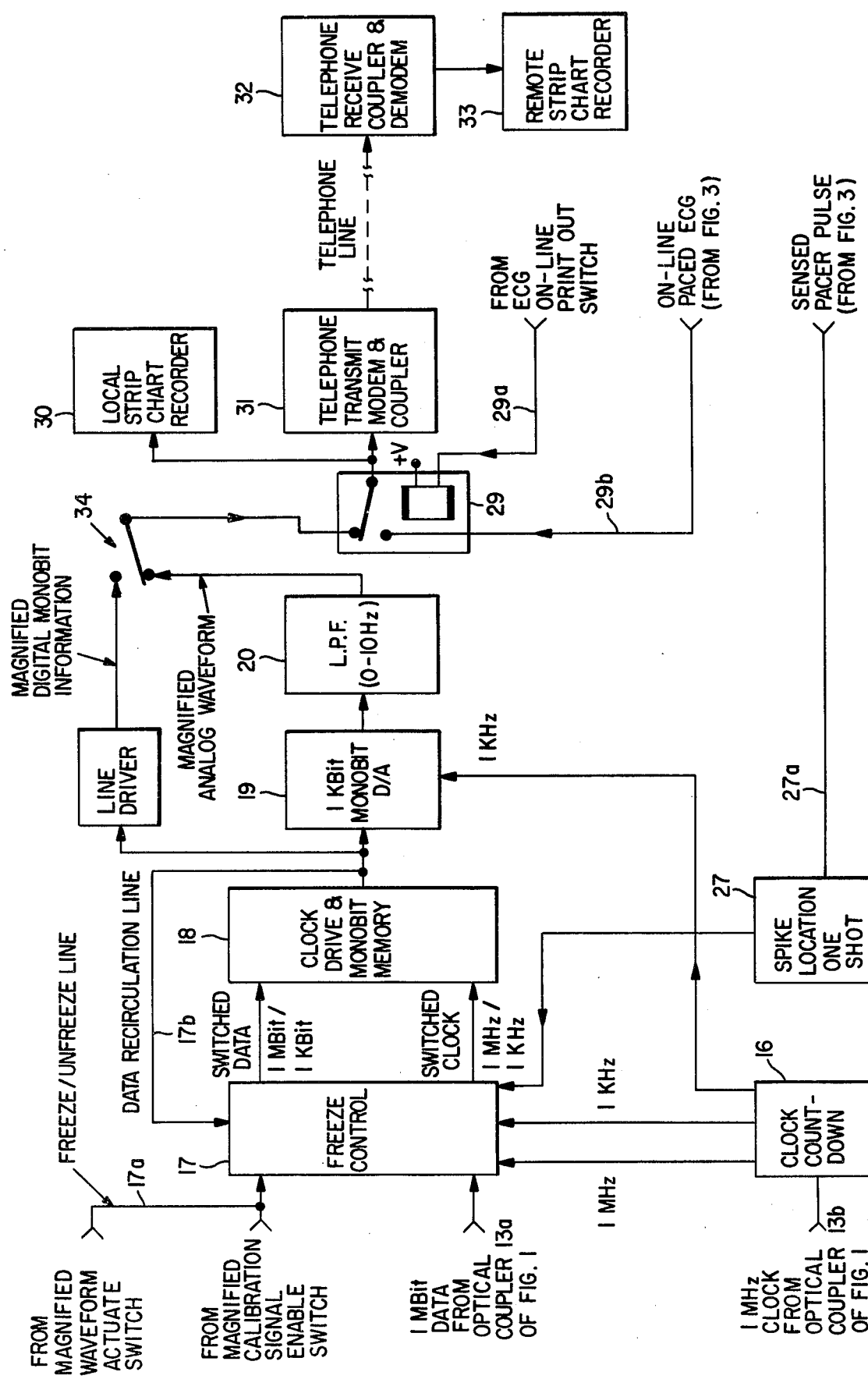
FIG. 2 is a block diagram illustrating the memory/magnification and output handling portions of this system according to the invention.

The 1 Mbit data output of optical coupler 13a and the 1 MHz crystal clock squarewave output from optical coupler 13b are fed to a memory freeze control stage 17 and a clock count/down stage 16 respectively of the magnification circuitry portion of the system as illustrated in FIG. 2. Freeze control stage 17 also has freeze-/unfreeze input line 17a leading from a control switch, which is further discussed hereinafter. Clock countdown stage 16 comprises a suitable earth-referenced clock shaping and countdown circuit with phase delay equalization between clock and data from the optical coupler 13 and synchronized clock countdowns of 1 KHz and 100 KHz.

Memory freeze control 17 provides two output lines, i.e. switched data 1 Mbit/1 Kbit and switched clock 1 MHz/1 KHz, to a clock drive and monobit memory stage 18. The output of memory stage 18 is in turn coupled back to freeze control stage 17 via a data recirculation line 17b. The output of memory stage 18 is also coupled to a 1 Kbit, monobit, digital-to-analog converter stage 19, which also receives a 1 KHz clock signal from clock countdown stage 16. The D/A converter stage 19 magnified analog waveform output is in turn coupled through a low pass filter (0-10 Hz) 20 and a relay arrangement 29 to either or both (as is particularly shown in FIG. 2) a local strip chart recorder 30 and a telephone transmission coupler 31. The latter, or course, enables transmission of the analog signal over the telephone lines (and through the telephone exchange) to a telephone receiver coupler 32, which enables the received signal to be suitably treated for presentation to a conventional gain-adjusted remote strip chart recorder 33.

Relay arrangement 29 in its normal position functions as above-described. However, upon actuation via line 29a leading from an ECG on-line printout switch (switch 64 of FIG. 3), relay arrangement 29 is caused to couple to the strip chart recorder 30 and (or) telephone transmitter coupler 31 the on-line paced ECG present on lead 29b, as derived from the circuitry of FIG. 3.

It is to be noted in FIG. 2 that provision is made for selecting for output and (or) transmission, in place of the magnified analog waveform from LPF 20, the magnified digital representation thereof via switch 34 and relay 29. In the case of transmission over the telephone, it is likely that a magnification of approximately 4000:1 rather than the example magnification of 1000:1 described herein would be used to effect optimum transmission of the magnified digital representation over the telephone.

Freeze control 17, upon "magnified printout" command appearing at the freeze/unfreeze input line 17a (from switch 66 of FIG. 3), stops the 1 Mbit data received from the optical coupler 13a from shifting through the memory 18 and then activates a 1 Kbit data recirculation for a 1000:1 slowdown (in the example system herein described), which, of course, means a time expansion (magnification) of X1000. It should be clearly understood that different magnification factors can be readily achieved within the scope of this invention.

The magnification circuitry portion of this system, depicted in FIG. 2, further includes a spike location one shot stage 27, input coupled with circuitry having as its primary function to sense the pacer pulse (i.e. the circuitry of FIG. 3), and output coupled to the memory freeze control stage 17. Upon a "magnified calibration" command (from switch 65 of FIG. 3), which on the one hand is coupled via line 10a to relay arrangement 10 (FIG. 1) and on the other hand to line 17a, or a "magnified waveform" command (from switch 66 in FIG. 3) appearing on line 17a, the spike location one shot 27 enables the freeze control stage 17 and memory 18 to freeze the pacer spike at the right time and location in the memory without losing or destroying bits captured in the memory.

Figure 3:
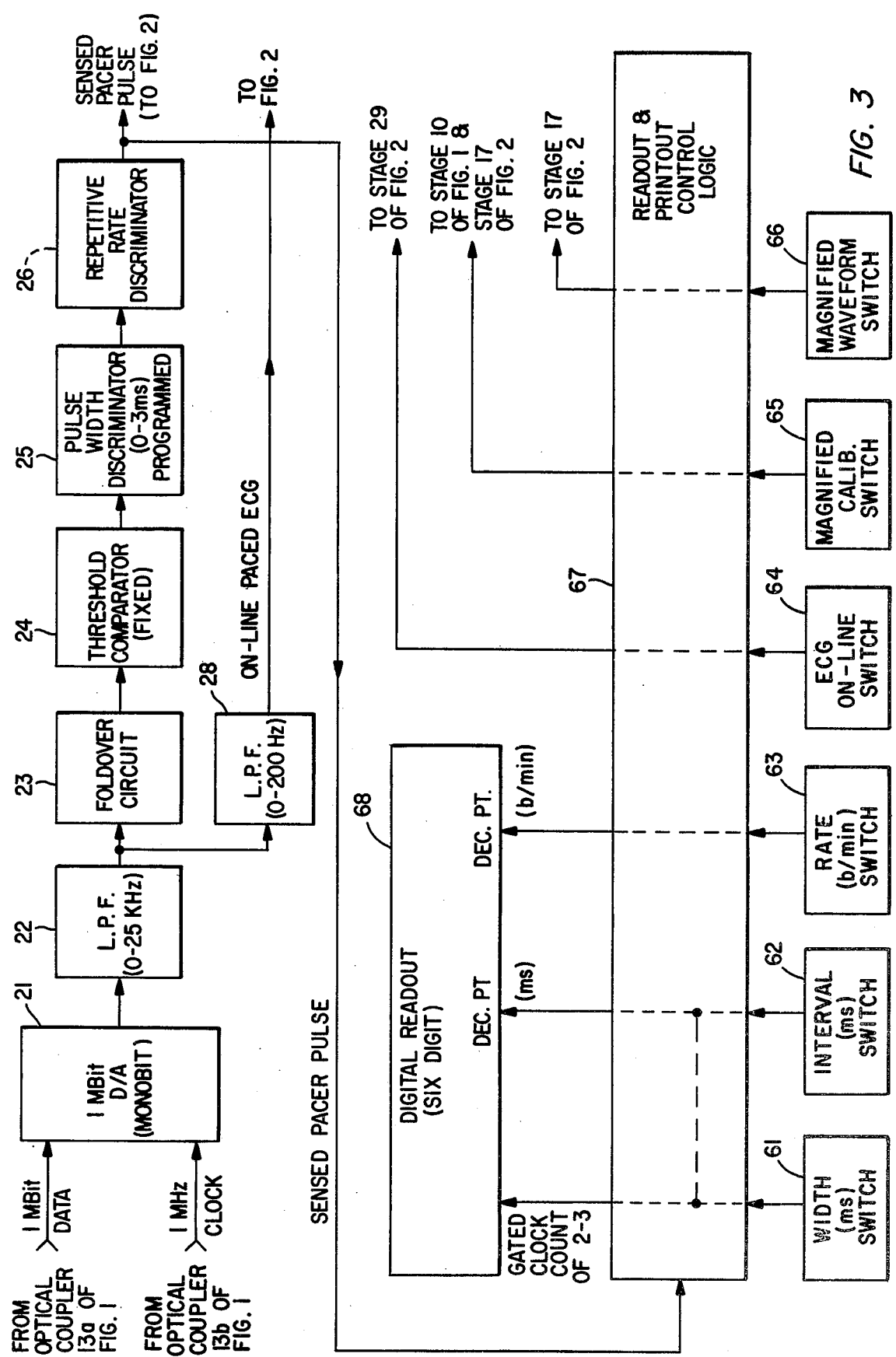
FIG. 3 is a block diagram illustrating the pacemaker device pulse sensing network and logic control portions of the system according to the invention.

The system according to the invention further includes a pacer pulse sensing portion which is depicted in FIG. 3. The 1 Mbit data and 1 MHz clock outputs from the optical couplers 13a and 13b respectively of FIG. 1 are fed to a 1 Mbit, monobit D/A converter stage 21. The output of D/A converter 21 is coupled through a 0-25 KHz low pass filter (LPF) 22 and a foldover circuit 23 to a fixed threshold comparator stage 24. The output of the 0-25 KHz LPF stage 22 also is passed through a second LPF (0-200 Hz) stage 28 to provide the on-line paced ECG output leading to the input 29b of relay arrangement 29 in FIG. 2.

The output of threshold comparator stage 24 is fed to a novel programmed pulse width discriminator (0-3 ms) stage 25, which provides the sensed pacer pulse output that is coupled to the spike location one shot 27 via input control line 27a in FIG. 2. The output of the pulse width discriminator (PWD) stage 25 optionally may be treated by a repetition rate discriminator stage 26, the output of which in turn provides the input to spike location one shot 27 (FIG. 2).

The pacer pulse sensing portion of the system as herein described with reference to FIG. 3, converts the digital data received from the optical couplers 13 via the 1 Mbit (delta-sigma) monobit D/A converter stage 21 and LPF stage 22 back into the same bandwidth analog signal as existed prior to being digitized at the output of the floating wideband amplifier 5, in FIG. 1.

The foldover (full wave rectifier) stage 23 passes all signal portions of positive polarity and inverts all signal portions of negative polarity, thus resulting in an output signal of positive polarity only. Positive and negative pacer pulses are thus recognized. This, of course, avoids, the need and cost of separate channels for positive and negative pacer pulses, but such is not to be considered beyond the scope of this invention.

As a result of the foldover stage 23, one comparator stage 24 with positive threshold bias is needed only. The latter stage is very vital in the elimination of all other waveform portions, such as the P, QRS and T waves of a paced ECG waveform. In addition, muscle tremor and noise spikes are also eliminated as long as their amplitude is below the threshold. Pacer spikes are at least 1-2 mVpp (bi-polar pacemakers), whereas their associated QRS complex is usually below 1 mVpp. However, in order to ensure that only the desired (pacer or calibration pulses) information is derived and presented at the output of the circuitry of FIG. 3, the 100 KHz-clocked, programmed digital pulse width discriminator stage 25 is provided, with a typical "window" of 0-3 ms and clock tolerance of, for example ±10 μsec (it should be noted that 1 μsec tolerance or any other suitable figure could be provided within the scope of this invention), and which will cut off through its time domain criterion anything else that is undesirable and which may have passed the threshold comparator stage 24. The PWD window criterion can be made variable through change of clock frequency and programming. The narrow pulse rate discriminator 26, as indicated, may be included with this circuitry.

By way of example, in the case of a unipolar pacemaker patient, the pacer spike at the patient's skin appears usually as a 20-30 mVpp pulse. In such a case, the calibrated attenuator 4 (FIG. 1) should be employed until the overload indicator light 6a goes out. A unipolar pacer pulse of 100 mVpp is usually accompanied by a QRS complex of 1-5 mVpp only. This 100 mVpp spike would probably overload the A/D converter stage 7 unless the attenuator 4 is moved until the indicator 6a does not blink anymore (which would amount to the attenuator [sensitivity switch] position of 50 mV/Cm, or an attenuation of x0.02). In this attenuated position the QRS complex is virtually totally invisible for the threshold comparator 24, and the PWD 25 merely passes a legitimate pacer pulse only. Again, a narrow range rate discriminator 26 could be added to eliminate eventual noise spikes of substantially the same amplitude as pacer pulses. However, the amplitude cutting action of the attenuator should not be overlooked.

Spike location one shot 27 (FIG. 2) acts upon the sensed pacer spike coming out of PWD stage 25 or pulse rate discriminator (PRD) stage 26 and sends a normalized, constant-width pulse to the memory freeze control 17. The latter is especially important in case of very narrow pacer pulses of 0.1 msec or less and assures a reliable freeze command.

Low pass filter 28, in series with LPF 22, cuts the bandwidth of the wideband paced ECG to 0-200 HZ, wide enough to recognize strong pacer pulses for an on-line, real-time paced ECG strip chart read-out. Of course, small and very narrow pacer pulses would not pass, and even if they did somehow pass the LPF 28, in all likelihood they could not be printed by a standard strip chart recorder which has an upper cut-off at 60 Hz or 100 Hz at the most.

Also included in FIG. 3 in block diagram form is an electronically interlocked readout and printout control 67 for a 6-digit display 68 of interval, width and rate. A typical interval display is 1000.02 ms (accuracy to ±10 μsec), a typical width display is 1.25 msec (accuracy to ±10 μsec), and a typical rate display is 60.0 b/min (accuracy to ±0.15%) or 0.1 b/min at 60 b/min rate).

The ECG pushbutton 64 activates relay 29 of FIG. 2; the magnified calibration pushbutton 65 activates relay 11 of FIG. 1 through isolation relay 10 (FIG. 1); and magnified waveform pushbutton 66 (as well as also switch 65) activates the memory freeze control 17 (FIG. 2). The width pushbutton 61 activates the digital measurement of the second pacer pulse out of say three pacer pulses, since the first pulse may be a noise pulse. For the same reason, the interval pushbutton 62 activates the digital measurement of the period between the second and third pacer pulses in the example here posed. The rate (b/min) pushbutton 63 activates the computation of the interval into a b/min rate. This latter function utilizes the teachings of U.S. Pat. No. 3,537,003.

The memory-magnification portion of this system according to the invention, as depicted in FIG. 2, shifts the digitized 1Mbit data from the optical coupler 13a through the freeze control circuitry 17 into the static shift register memory 18 under synchronized clock control of the clock countdown circuitry 16. Due to the fact that the system utilizes the 1 Mbit delta-sigma modulation technique (see e.g. U.S. Pat. No. 3,587,087), the memory 18 can be kept small, depending on the "window" of the PWD stage 25 (FIG. 3). For example, a 6Kbit memory and 0-3 msec PWD window allows the capture of pacer pulses from 0.01 msec to 3.0 msec width since the PWD 25 has a fixed delay of three msec in this case.

The unique pulse width discriminator stage 25 employed herein, does not change the pacer pulse width, and provides no output if the pacer pulse exceeds its upper window limit (3 msec in this example). Prior art PWD's, of course, have the same window criterion, but any pulse passed thereby loses its original width and has varying delay.

In the case herein described, the pacer pulse is always captured (frozen) at the same location, thus keeping the memory at a minimum. In addition, since the PWD 25 output maintains the original width, it can be used for digital, on-line, real-time measurement of the pacer pulse width, independent of the magnified printout process.

Upon magnified calibration command (switch 65 of FIG. 3) or magnified waveform command (switch 66 of FIG. 3), to the readout/printout control logic 67 in FIG. 3, the memory shift register clock of 1MHz from stage 16 is stopped and immediately switched to 1KHz. In addition, the recirculation path 17b between memory 18 and freeze control 17 is closed and the memory 18 disconnected from the input arriving from optical coupler 13a. The 1Kbit, monobit, delta-sigma D/A 19 together with low pass filter 20 converts the slowed-down recirculating memory content into a time magnified (X1000 in this example (analog waveform of highest fidelity regarding waveform (leading/trailing edge amplitude, plateau, decay, rise and fall times).

Upon ECG command via switch 64 of FIG. 3, the relay arrangement 29 of FIG. 2 connects local strip chart recorder 30 and (or) telephone transmit coupler 31 to LPF 28 (FIG. 3) and prints out the patient's on-line paced ECG (which may be demand paced or fixed paced or spontaneous heartbeats). For this on-line, real-time, paced ECG printout, the attenuator switch 4 (FIG. 1) will in the example depicted herein probably be either at 1 mV/cm (equivalent to ECG preamp gain of X1000 or 2 mV/cm (equivalent to gain of X500). The associated pacer spike will cause the overload indicator 6a to blink at the pacer pulse rate. It is again noted that the system herein contemplated can handle larger pacer pulses of up to 1 Vpp accompanying the QRS. In this mode of operation, pacer pulses larger than the power supply at the preamplifier stage 5 are clipped anyway, and thus do not cause harm to any circuitry, and their printout amplitude is a function of LPF 28 bandwidth and upper frequency cut-off of local recorder 30 or remote recorder 32.

Upon magnified calibration or magnified waveform command, from switch 65 or switch 66 respectively, relay 29 is arranged to connect local strip chart recorder 30 and (or) telephone transmit coupler 31 to LPF 20. Thus, there may be effected the printout of the internal 1 KHz squarewave with a time magnification of X1000 in order to allow gain adjustment at the telephone receiver side. Since the internal calibration is injected through relay 11 of FIG. 1 in reciprocal value to the attenuator 4 setting (that is, for example the 100 mV/cm sensitivity switch 4 setting, the attenuation is 10:1, the total preamplifier stages 2, 3 and 5 gain in thus effectively only X100; therefore the calibration injection is 10 mVpp resulting in a 1 vpp squarewave at the A/D stage 7 input, the printout at the local recorder 30 and/or remote recorder 32 without telephone transmission losses will be exactly 1 vpp/cm. The reciprocal calibrating injection thus provides the same calibration printout voltage (i.e. 1 vpp/cm in any attenuator position. This feature provides, therefore, a fast, easy way of calibrating the system in the face of virtually any kind of transmission system loss and thus assures a high fidelity hard copy of a patient's pacemaker pulse, perhaps thousands of miles away.

Looking again to relay arrangement 12 in FIG. 1, there is provided thereby, in addition to an avoidance of "hang-up" of amplifier stages 3 and 5 during lead switching, quick return of the A/D stage 7 and memory 18 to normal, and thus fast return of the graph recorder baseline (in case of lead switching and/or skin voltage).

Figure 4:
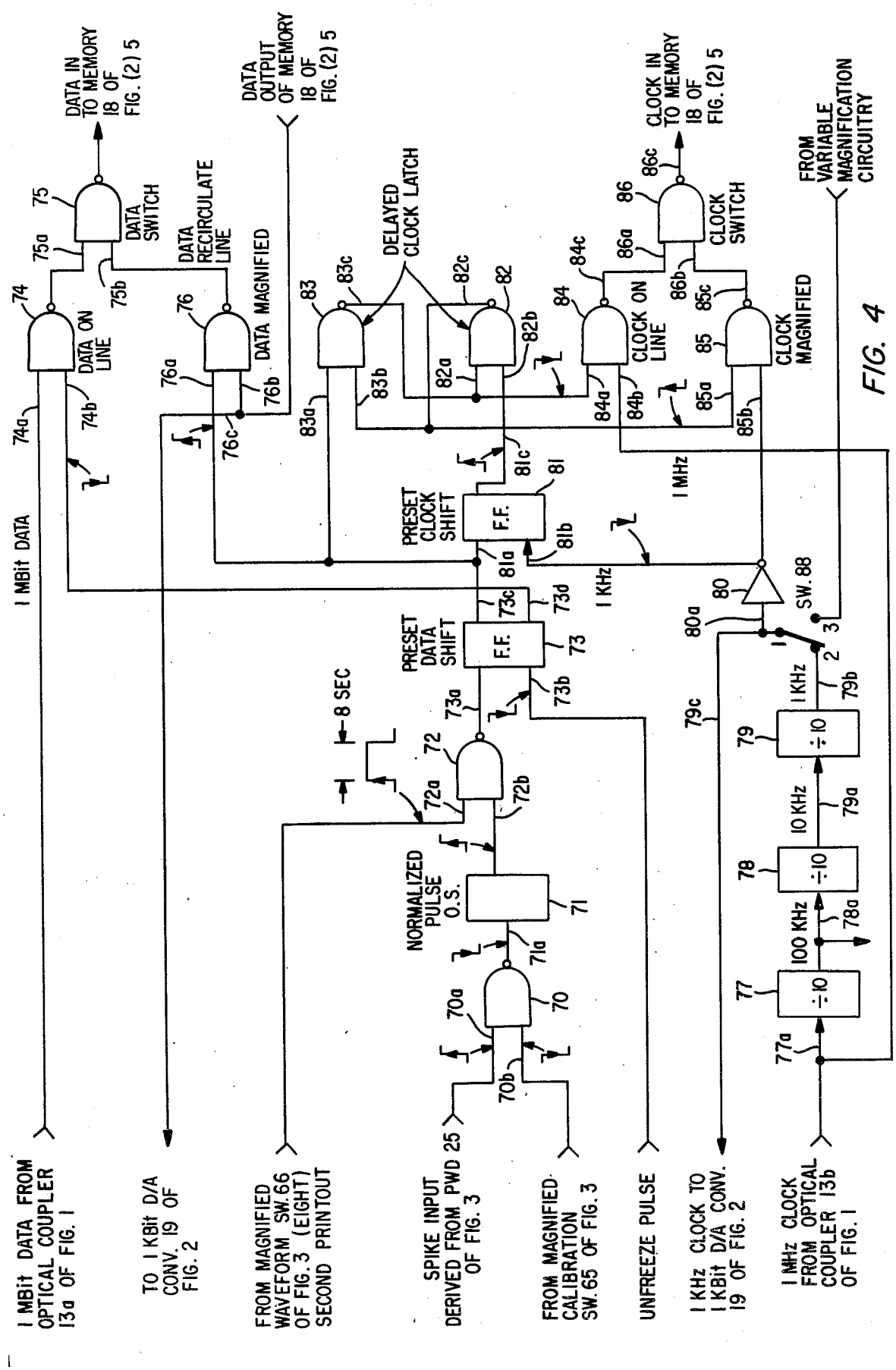
FIG. 4 is a logic diagram of circuitry contained in blocks 16–17 and 27 of FIG. 2.

Reference is made to FIG. 4 in which there is depicted specific logic for stages 16, 27 and, in particular, the memory freeze control stage 17 of FIG. 2. Elements 77-80 comprise clock countdown stage 16; the spike location stage 27 in the example depicted in FIG. 4 is comprised of element 71 and the input thereto via gate 70; the remainder of the circuitry of FIG. 4 comprises the freeze control logic stage 17.

Figure 5:
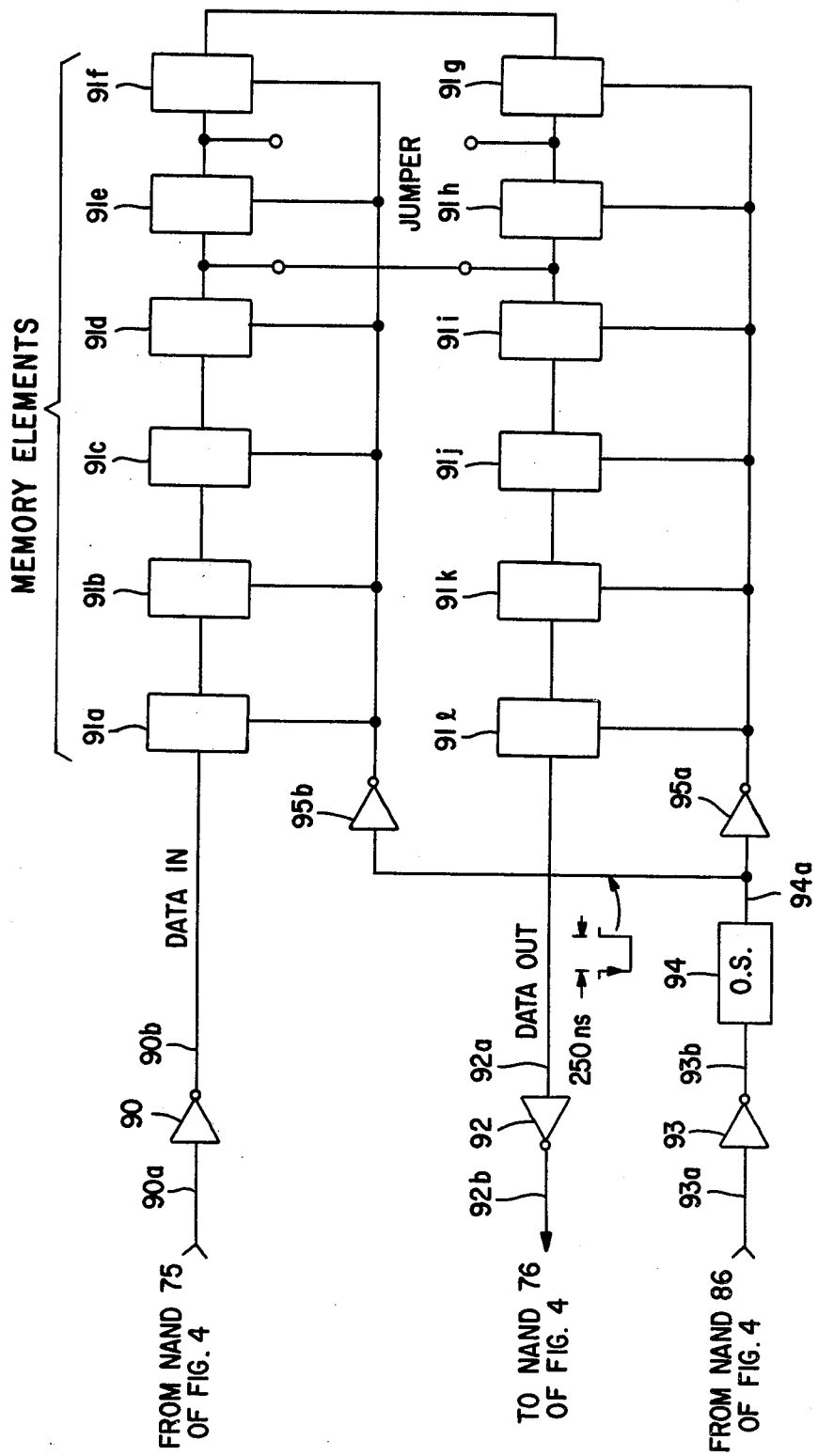
FIG. 5 is a logic diagram of circuitry contained in block 18 of FIG. 2.

In the "non-magnified" mode of operation, the 1Mbit data from optical coupler 13a of FIG. 1 is fed to "data on-line" Nand gate 74 (FIG. 4) which passes same on to a data switch Nand gate 75 and on to the memory 18 of FIG. 2 (and FIG. 5). The data circulates from element to element in memory 18 of FIG. 5, with the output thereof appearing on line 76c (FIG. 4), which in turn is coupled to the 1Kbit D/A converter stage 19 of FIG. 2.

When it is desired to print-out a magnified portion of the pacer waveform (or the calibration injection signal), the data flow stream as described above is changed, and the clocking of stage 18 is also changed under the control of memory freeze control stage 17, in effecting the expanded or magnified print-out. Assuming the operator wishes to observe an expanded print-out of the pacer waveform, he merely actuates the magnified waveform push-button switch 66 (FIG. 3) which, via the control logic circuitry 67, causes a positive-going pulse to be generated having a fixed duration of for example eight seconds. In FIG. 4, this pulse is in-coming on line 72a to Nand gate 72. Meanwhile the pacer sensing channel circuitry of FIG. 3 has continued to operate with the PWD stage 25 developing delayed pacer pulses (in the example hereinbefore described the delay in 3 ms, constant for each pulse), which as shown in FIG. 4, are positive-going pulses arriving on line 70a at one input of Nand gate 70. The arrival of a pacer pulse causes gate 70 to be enabled, which in turn activates one-shot 71. One-shot 71 normalizes the sensed and delayed pacer pulse as to amplitude and width. The combination of a positive-going output pulse from one-shot 71 on line 72b and the fixed (eight seconds) magnified waveform actuate pulse on input line 72a of Nand gate 72 causes the latter to generate a negative-going pulse on input line 73a to preset data shift flip-flop 73 (originally reset by an "unfreeze" pulse on line 73b).

Figure 6A:
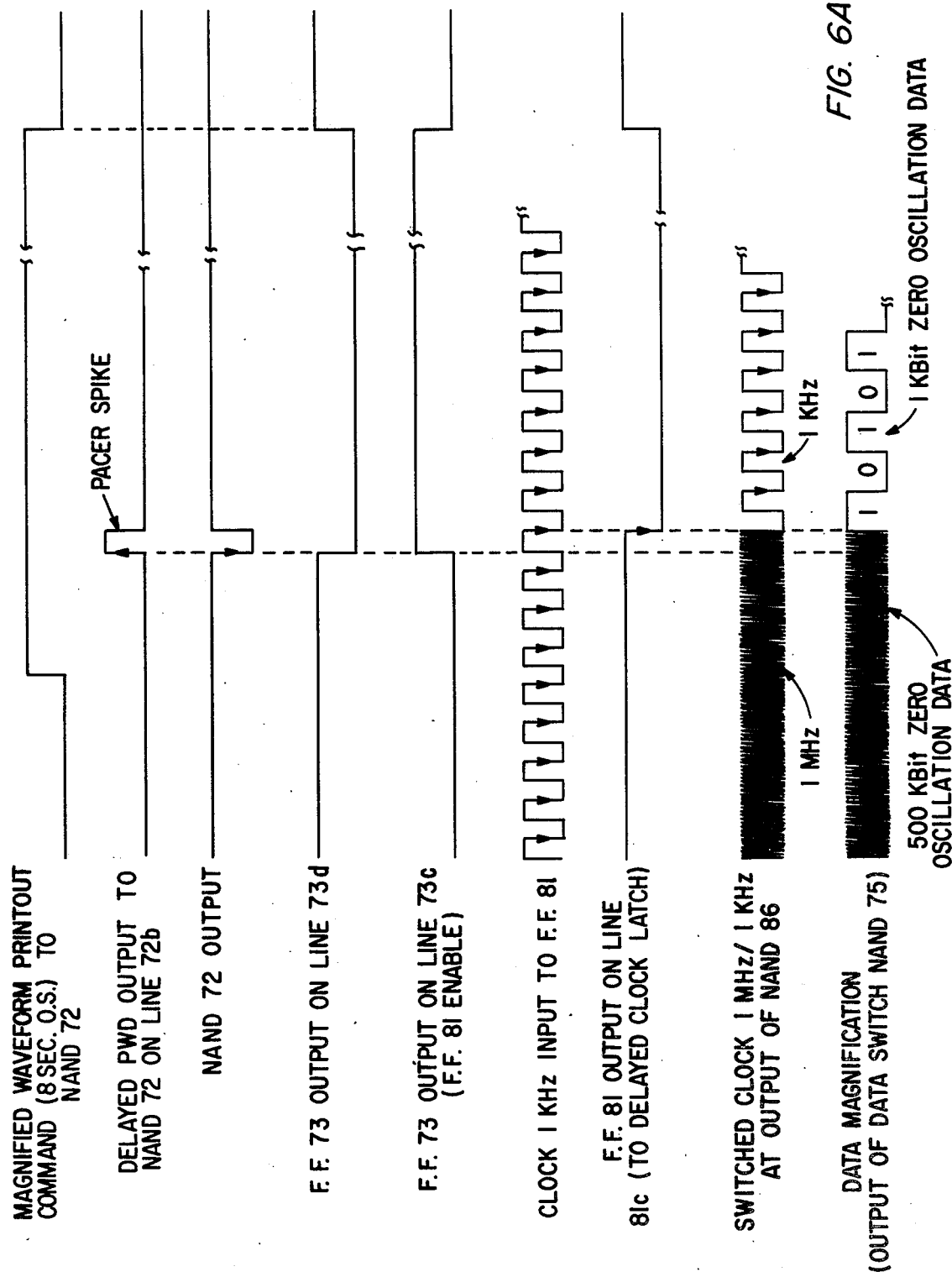

The operation of the logic circuitry described herein in reference to FIG. 4 is represented in timing diagram form in FIGS. 6A and 6B, which may be consulted for a better understanding of the memory freeze control. From FIG. 6A, it may be seen that a negative-going pulse output from Nand gate 72 represents not only that the operator desires to see a magnified pacer waveform spike, but also that a pacer pulse is present in the memory 18 (FIG. 5) and that its location in the memory is known. The PWD stage 25 output to Nand gate 70 and ultimately to Nand gate 72 confirms that a pacer spike is in the memory. It was stated above, in reference to the example herein described, that the delay provided by the PWD stage 25 regarding the pacer pulses in 3 ms (and constant for each pacer pulse), i.e. if a pacer spike passes the PWD 25 it has to be less than the upper limit of the PWD "window", which is 3 ms. In the example depicted, the memory 18 cycle time at a 1 MHz clock control is 6 ms; thus, any pacer pulse of 3 ms or less would automatically be present in the memory during the time that pulse takes to also pass the PWD stage 25 of the pacer sensing channel, and would be locatable in the memory during this time and before it cycles out of the latter and is lost.

With FF 73 activated (set) by Nand gate 72, the Q output thereof on line 73d is fed via line 74b to data on-line Nand gate 74, causing the latter to block any further data on line 74a from entering the memory 18 via data switch Nand gate 75. FF 73 in the set stage provides several other functions. Its Q output on line 73c is coupled via lead 76a to data magnified Nand gate 76, causing the latter in turn to "close", thus establishing the data recirculation path which comprises the memory 18 (FIG. 5), Nand gate input line 76b, Nand gate 76, Nand gate input line 75b, data switch Nand gate 75 and back to the memory. It may be seen in FIG. 6A that whatever data was present in memory 18 when FF 73 became set is then continuously recirculated for a time at the clock rate of 1 MHz. The data is circulating at a 1 Mbit rate, as the 1 MHz clock is arriving at and controlling memory 18 via optical coupler 13b (FIG. 1), clock on-line Nand gate 84 (by way of input line 84b) and clock switch Nand gate 86 (by way of lead 84c, 86a).

A third function of FF 73 is to provide its Q output to preset clock shift flip-flop 81 via pre-set line 81a. Up to now, only "data switching" (i.e. recirculation at the 1 MHz rate) has occurred; the clock switching necessary to derive the expanded waveform will now be described. The clock input to FF 81 from inverter 80 casues a low-to-high transition to occur on output line 81c of FF 81 leading to delay clock latch Nand gate 82 via input lead 82b.

The final aspect of FF 73 is that its Q output on line 73c is also coupled via line 83a to delay clock latch Nand gate 83.

The priming conditions of the memory freeze control logic for switching the clock from 1 MHz to 1 KHz, entirely in sync., are now present. In order for an orderly transition in the two clock rates to occur, the switching to the 1 KHz rate must occur in synchronism with the 1 MHz rate; otherwise there will result in the memory a condition which may be called "bit collision", and ultimately the information in the recirculating memory will become lost. FF 81 in essence provides a proper delay in the clock switching until such time as the 1 KHz clock input thereto via line 81b is synchronous with the 1 MHz clock. In this regard, the 1 KHz signal is always present at the line 81b input FF 81 via the clock countdown circuitry comprising elements 77-80, in which the 1 MHz clock from optical coupler 13b is received on line 77a and the same is divided in three ÷10 stages 77-79 to yield the 1 KHz signal. This is then passed through a switch 88 and inverter 80 to FF 81.

The problem to be overcome essentially is that in order to obtain a magnified waveform, the 1 MHz clock (1 μsec.) must be stopped and transformed to a 1 KHz (1000 μsec.) without causing bit collision and loss of information. To do so it must be assured that in the transformation from the high to the low clock rate the logic picks up synchronously the exact next clock pulse following the clock switching. This may be better seen with reference to FIGS. 6A and 6B, particularly the latter.

It is to be noted that the clock-switching example illustrated in FIG. 6B is for convenience from 1 MHz to 100 KHz, rather than 1 MHz, as the latter could not be adequately shown in the space of a single drawing, whereas the 100 KHz switching example is readily depicted in the single drawing. It is to be understood that this choice of example is solely for the ease of illustration and convenience and that the principles of switching and the care required to be taken so as not to lose memory information during switching are all equally applicable in the case of 100 KHz clock switching as for the 1 KHz clock switching example.

FF 81 provides, as aforesaid, an automatic delay between the input pulse arriving at line 81a and the next high-to-low transition of the 1 KHz input on line 81b. This ensures proper switching of the clock so as to avoid a phase-in or phase-out collision between the clock pulse and the data switching from stage to stage in the static memory 18. This is, one is assured that the new clock (1 KHz) is synchronized with the phase-in/phase-out of the previous (1 MHz) clock.

FF 81, then, provides at the proper time the output to the delayed clock latch (Nand gates 82, 83) on line 81c, which causes the clock on-line Nand gate 84 to block the 1 MHz clock going to the static memory 18 (via gage 86) and to pass the 1 KHz clock through clock magnified Nand gate 85, the output of which gate is passed through the clock switch Nand gate 86 and on to the static memory 18.

With zero volt input signal, the delta-sigma-modulation A/D converter 7 sends out a so-called "zero-oscillation data" stream at a 500Kbit rate. Assuming such a zero oscillation data stream (FIG. 6B) from the 1MBit per/sec. monobit A/D converter 7, one has a 1MBit data stream of alternating zeros and ones (with the "ones" [and also the "zeros"] appearing at the 500KBit rate), each bit being 1 μsec. wide as shown. At this rate, the clock driver supplies phase-in ($\phi_{in}$) and phase-out ($\phi_{out}$) pulses to the memory before freeze.

Now, with the pulse from line 73c of FF 73, the preset input of FF 81 is enabled. With this input being low, a clock pulse of the 1 KHz waveform on line 81b cannot set, but rather can only clear FF 81; thus, in that event FF 81 would stay cleared. With the line 81a input to FF 81 going high, the next clock pulse negative transition from the 1 KHz signal will toggle FF 81, and its output goes high, thus setting latch Nand gate 82, which in turn enables Nand 85 for passing the 1 KHz clock on to memory 18 and also disables Nand 84.

As stated before, the example of FIG. 6B involves a switch-over from 1 MHz to 100 MHz in order to show how the switch-over proceeds, since 1000 clock pulses (which would be needed for illustration of a 1 MHz to 1 KHz change) cannot adequately be shown on a single drawing.

At the freeze command of FF 81 (top waveform in FIG. 6B), a phase-in ($\phi_{in}$) clock pulse is followed by a phase-out ($\phi_{out}$) clock pulse; otherwise a mixup of memory bits would occur. The 1 MHz and 1 KHz clocks have to be of the same phase.

In the example given in FIG. 6B, the 500 Kbit (1 μs per bit) stream of alternating zeros and ones has now become a 50 Kbit (10 μs per bit) stream of alternating zeros and ones (or a x10 magnification in time). The preferred example for the pacer diagnostic system however is, as aforesaid, a X1000 magnification through clock switching from 1 MHz to 1 KHz.

At the end of the eight sec. print-out (effected by the eight-second pulse from actuation of switch 66), the memory content is destroyed and the memory refilled with a new data stream of 1 Mbit within 6 ms. The various flip-flops and latches are reset at the same time.

Attention is called to the fact that in the 1 KHz countdown line is switch 88 which may be actuated to switch a clock signal to FF 81 of other than the fixed (1 KHZ) frequency. That is, through suitable conventional logic, and perhaps a further select switch, various different clock frequency signals may be supplied to pin 3 of switch 88, thus offering to the operator a series of different magnifications on the hard copy print-out.

Looking to the logic circuitry of FIG. 5, which comprises the static memory 18, the information therein recirculated upon actuation of the magnified waveform switch 66 (FIG. 3) along the data recirculation path described above in connection with FIG. 4, which takes the information from the memory at the output of the latter at inverter 92 and returns the information to the memory via inverter 90. The second phase in providing a magnified waveform, i.e. the clock switching phase, that occurs as described above regarding FIG. 4, concerns the input to the memory which includes inverter 93, wherein the clock control signal in turn is coupled to a one-shot stage 94, which is a fixed period clock driver (in order to have the same clock pulse width for different shift rates), and from there to to inverters 95a and 95b, to be passed on to the various memory elements 91(a)–91(l). FIG. 5 includes a jumper between elements 91(d) and 91(l) indicating that any suitable size memory is possible, and that more or less of the elements 91(a)–91(l) may be used for a particular time desired in which the information normally would circulate through the memory.

It should be noted that the recorder (e.g. local strip chart recorder 30) may be coupled so as to start when the magnified waveform or magnified calibrate switches 66 and 65 respectively are actuated. In the preferred arrangement herein described, the same signal actuates the recorder 30 as assists in locating the position of the pacer spike in the memory (i.e. the eight-second input pulse to Nand gate 72 [FIG. 4] on line 72a).

Figure 7:
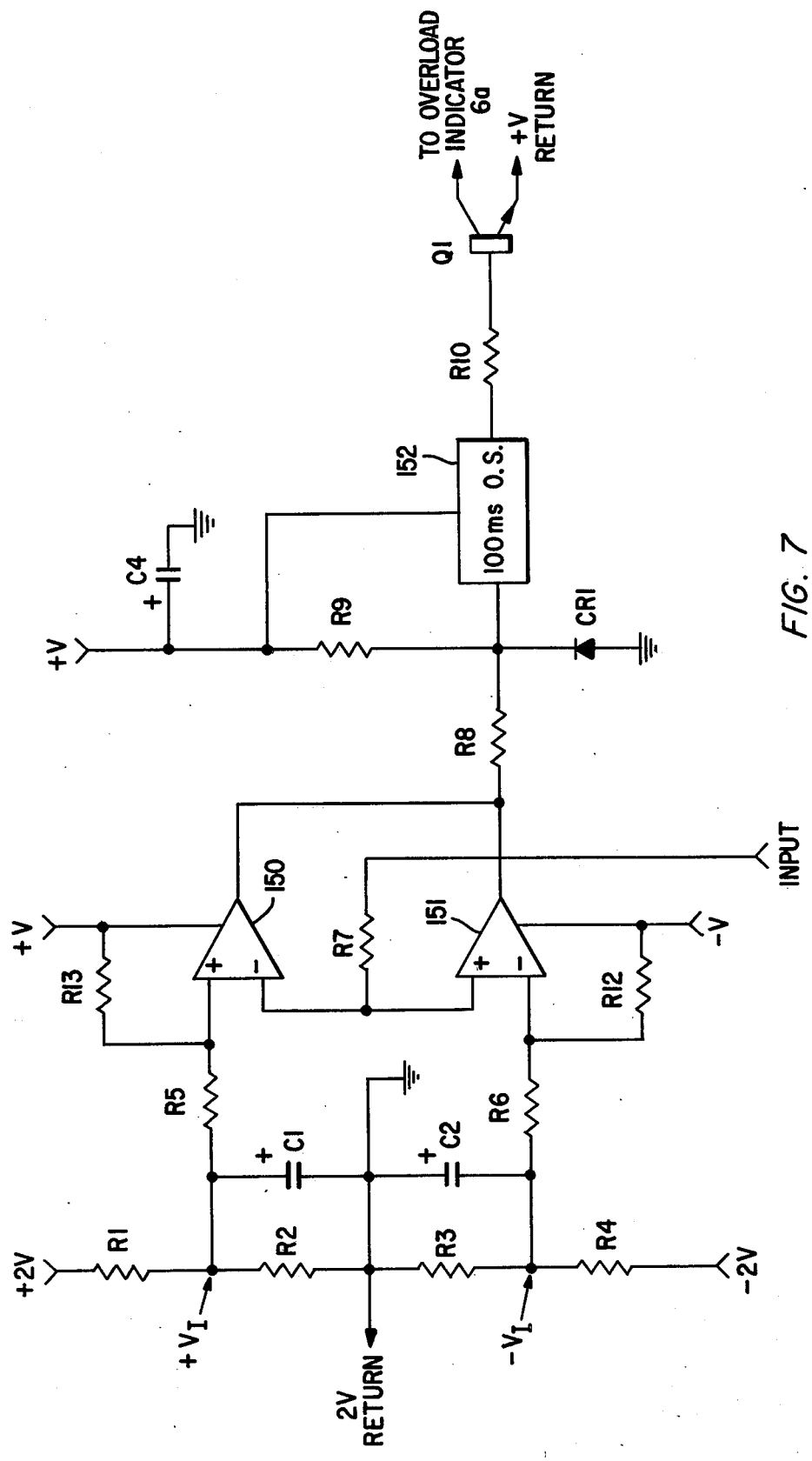
FIG. 7 is a schematic diagram illustrating circuitry contained in block 6 of FIG. 1.

Reference is now made to FIG. 7 which illustrates in schematic form the circuitry of overload indicator circuit 6 (of FIG. 1). Essentially, a voltage divider network R1–R4 is provided to derive a specific reference or threshold voltage $|V_I|$ shown to be present in FIG. 7 as $+V_I$ between R1 and R2 and $-V_I$ between R3 and R4. These reference voltages are coupled to respective first inputs of a pair of comparators 150, 151, the outputs of which are "ORed". The analog output of preamplifier 5 (FIG. 1) is coupled into the circuitry of the overload indicator where marked as "input". If the level of the pacer spike injected at "input" is greater than $|V_I|$, then the appropriate one of the comparators will provide an output causing one-shot 152 to fire and the overload indicator lamp 6a to light.

It should be noted that the pacer spike may or may not be equal in amplitude to the QRS wave. Moreover, the pacer spike may be positive or negative-going. It is because of this latter factor that two comparators 150,151 are provided, one for positive incoming pacer spikes and one for negative incoming pacer pikes.

The threshold voltage $|V_I|$ is selected at a value somewhat below which the A/D converter stage 7 (FIG. 1) would overload. This provision is made in the apparatus according to the invention to ensure fidelity of the pacer spike (i.e. to avoid clipping).

Adjustment of the sensitivity switch 4 (FIG. 1) until the blinking lamp 6a is extinguished ensures that the input to the A/D stage 7 is less than overload amplitude. By the position of the sensitivity switch 4, it is ensured also that there will be no clipping occurring in the preamplifier stage 5. Once the blinking lamp 6a (indicating overload) goes out (by virtue of an adjustment of sensitivity switch 4), it can be said that the equipment has been normalized relative to the patient.

One further factor is ensured by the reference voltage $|V_I|$ and a satisfactory adjustment of the sensitivity switch 4 (such that the blinking overload light 6a is extinguished), namely that the output of the recorder (e.g. local strip chart recorder 30) will cause a print-out which will with certainty be within the range of the dynamic recorder. Thus, the entire pacer spike will be accurately displayed.

The problem, however, of a visual indication of overload based on the pacer spike input itself (normally the pacer spike is of considerably higher amplitude than the QRS wave and thus it would be the input analog waveform factor which would trigger overload) is that the pacer spike is normally possessed of only a 1 or 2 ms pulse width. This is insufficient to activate the lamp 6a to give a visual indication of overload. Therefore, in FIG. 7 provision is made to remedy this problem in the form of the inclusion in the overload indicator circuitry of a one-shot 152 (of 100 ms duration) which is operatively coupled to the output of the dual comparators 150, 151. The on-shot 152 output is in turn coupled via a transistor stage Q1 to the visual indicator 6a.

The effect of one-shot 152 is to provide a normalized pacer pulse of 100 ms in duration, which provides enough time to fully illuminate the lamp 6a, thus enabling an overload condition base on the very narrow pacer spikes to be visually represented. There is little concern caused by normalizing the pacer spike to 100 ms, as the rate of the pacer is normally such that the next pacer spike arrives in the area of one second after the previous spike, which leaves more than sufficient time for spike normalization, as here, in the area of 100 ms.

This overload indication circuitry/sensitivity switch arrangement essentially represents a manual AGC arrangement which automatically provides an error readout visually.

One other very important aspect of the overload arrangement, is that the overload indicator 6a when blinking (i.e. representing an overload) does so at the pacer rate. That is, the indicator in an overload condition blinks at the rate at which the pacemaker is producing pacer spikes. Thus, a visual indication of the pacer rate is provided to the operator.

To summarize the overload circuitry features, there is provided a physical (visual) indication that an overload for the A/D converter 7 exists, and that sensitivity switch should be changed to a higher attenuation. There is ensured that the floating front end A of the pacer diagnostic analyzing system is operating at the proper quiescent level for the various sections of the system to ensure fidelity of the waveform. This means an instant verification of the entire ECG (pre-amp) front end, including the patient electrode hookups and also the on-line buffers (voltage followers) 2 in FIG. 1.

The attenuator and calibration is comprised of a countdown chain and a control gate with divider. The attenuator switch is arranged in such a manner to provide a reciprocal function in the ECG amp. Actually two divider networks are employed, one for the calibration and the other for the ECG. amp. The idea is to provide a constant one volt peak-to-peak calibration signal at the final output of the ECG amp, regardless of the sensitivity switch position. This is achieved for example by providing two decks on the sensitivity switch. Deck "A" is used for the calibration attenuation and deck "B" for the ECG amp attenuation. As the attenuation on deck "A" increases, the attenuation on deck "B" decreases or vice-versa. It should be noted that deck "A" is only in the circuit when the calibration button is depressed which activates relay 10, which in turn activates floating relay 11. Relay 11 disconnects amplifier 3 from the on-line ECG buffers (volgage followers) 2 and connects amplifier 3 unbalanced to the reciprocal calibration attenuator 4.

The system is designed to provide a 1 KHz calibration signal at a defined amplitude of one volt peak-to-peak when the calibration switch is depressed. This signal is applied to the input of the first ECG amplifier and will "check out" the entire pacer diagnostic system including readout and print-out. This assures the operator that the entire system is in working condition. Regardless of any sensitivity switch position, the magnified calibration print-out (it is emphasized) is always 1 Vpp/cm.

It is to be equally emphasized that the magnified calibration print-out is employed to assure the operator that the entire system waveform expansion is also precisely correct from a time standpoint. That is, this calibration vehicle provides also a precise time validity check on virtually the entire system. It does so by providing a frequency reference, crystal-controlled clocking coupled into the front end of the system, which is processed through the system and expanded. There is provided in the principle example depicted herein a crystal-controlled expanded 1 KHz (initially 1 ms.) squarewave of 1 Hz at the recorder. For example, assuming a recorder speed of 25 mm/per sec. (1 mm=40 ms) and with this 1000:1 time magnification, 1 mm represents 40 μsec. This means that from leading edge to leading edge of each cycle of the calibration squarewave, there will be a correspondence to 25 mm on the recorder print-out.

Reference is now made to FIGS. 8 and 9A-9F in which there is depicted the circuitry and operation of a unique pulse width discriminator (PWD) capable of performing the functions hereinbefore described with reference to PWD stage 25 in FIG. 3.

In the following, the example of PWD described has for its "window" 0.1 ms–5 ms, as opposed to the window consideration of 0–3 ms hereinbefore given with respect to PWD stage 25 in FIG. 3. It is to be understood that the basic features of this unique PWD, illustrated in detail in the following description referenced to FIGS. 8 and 9A-9F, are nevertheless representative of an example of PWD which is readily capable of performing the functions intended of PWD stage 25. The only modification needed in the remainder of this system for a PWD having a window upper limit of 5 ms would be to expand the memory stages 18 to ensure a normal circulation time of greater than 5 ms. This, of course, may be easily accomplished by moving the jumper further to the right in the schematic drawing of the memory in FIG. 5.

Figure 8:
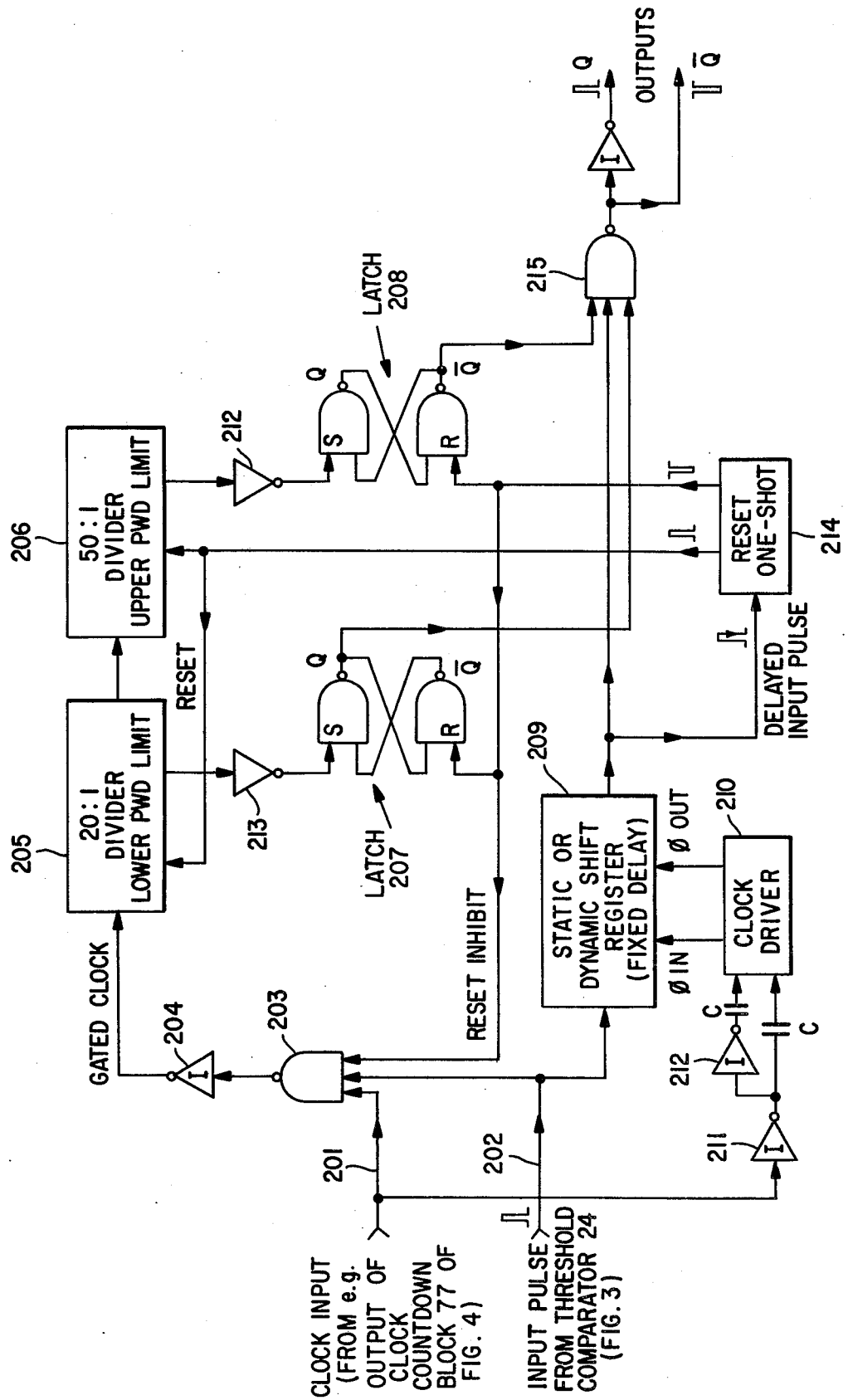
FIG. 8 is a block diagram of circuitry contained in block 25 of FIG. 3.

The PWD of FIG. 8 is of one hundred percent digital, completely clocked design. The pulse width window tolerance at the lower side is a function of a clock period only. It is to be understood that the lower side of the window may be dropped altogether to obtain a window of say 0–5 ms, similar to the 0–3 ms window as hereinbefore mentioned. The pulse width tolerance in this example of PWD (FIG. 8) is slaved to the clock period chosen in reference to the window tolerance at the lower side. And very important, the output pulse width is identical to the input pulse width (within the clock period tolerance). Equally important is the fact that the output pulse has a constant delay equal to the upper limit of the PWD window.

It is to be further understood from the above that the PWD of FIG. 8 is "programmed" (as indicated in block 25 of FIG. 3) in that with the FIG. 8 circuitry being of completely clocked design, the "window" may be changed simply by changing the clock input to a pulse repetition rate which would yield the desired window.

The PWD circuitry of FIG. 8 is perhaps most easily described with reference to an assumed clock of 100 KHz (which may be derived from the output of clock countdown stage 77 of FIG. 4) incoming on line 201, and an input pulse of 2 ms width incoming on line 202. The latter is coupled to the input of a static or dynamic shift register 209 wherein it is delayed over a fixed period of time. A 500-bit shift register is here assumed. The delay is therefore 500 bits times 10 $\mu$s clock period (100 KHz clock, T=10 $\mu$s) which=5 ms. The clock is received by shift register 209 via an inverter 211, 212 combination and a clock driver circuit 210. The maximum possible delay tolerance is one clock period, or a delay accuracy of 0.2% maximum.

The 100 KHz clock and 2 ms input pulse are also coupled to a Nand gate 203 which gates the 100 KHz, 50% duty cycle clock with the 2 ms input pulse and with a reset inhibit pulse which originates from reset one-shot stage 214. One-shot 214 provides this output reset pulse to Nand gate 203 upon receiving a delayed input pulse from shift register 209.

The output of Nand gate 203 is connected via inverter 204 to a 20:1 frequency divider arrangement for the lower PWD limit function, i.e. in this example a frequency reduction to 5 KHz, 50% duty cycle for lower latch 207. The 20:1 divider 205 is coupled to lower-limit latch 207 via an inverter 213. Since the 5 KHz squarewave period is 50% a digital 0 and 50% a digital 1 for 0.1 ms each, there is obtained a trigger for the 0.1 ms latch, i.e. latch 207, which occurs 0.1 ms after the leading edge of the input pulse. Therefore, latch 207 enables output Nand gate 215 only after 0.1 ms, or the lower pulse width window limit. Coupled to divider 205 is another counter arrangement wherein a frequency division of say 50:1 takes place for the upper PWD limit. Together with the 20:1 frequency division, there is thus obtained at the output of divider 206 a 1000:1 frequency division or a 100 Hz, 50% duty cycle squarewave, whose period is 50% a digital 0 and 50% a digital 1, each 5 ms long. There is thus obtained a trigger for the PWD window upper-limit latch 208, i.e. the 5 ms latch, which trigger occurs 5 ms after the leading edge of the input pulse.

Latch 208, when set, disables output Nand gate 215 only 5 ms after the leading edge of the input pulse, and therefore establishes together with the fixed delayed described above in connection with the shift register 209, the upper pulse width window limit of 5 ms in this example.

At the trailing edge of the 5 ms delayed input pulse from shift register 209, reset one shot 214 resets all counters (205, 206) and latches (207, 208) and also inhibits input Nand gate 203 in order to prevent competition between counter resetting and counter start-up. Were it not for the possibility of "overshoot" occurring in the paced ECG waveform (immediately following the pacer spikes) the reset one-shot 214 output pulse ideally would be smaller than one clock period. However, in order to avoid complications resulting from the existence of overshoot and also the QRS complex, it is to be understood that it is within the scope of this invention to provide a reset output pulse (inhibition pulse) for example of up to 300 ms, or even greater duration.

Figure 9A:
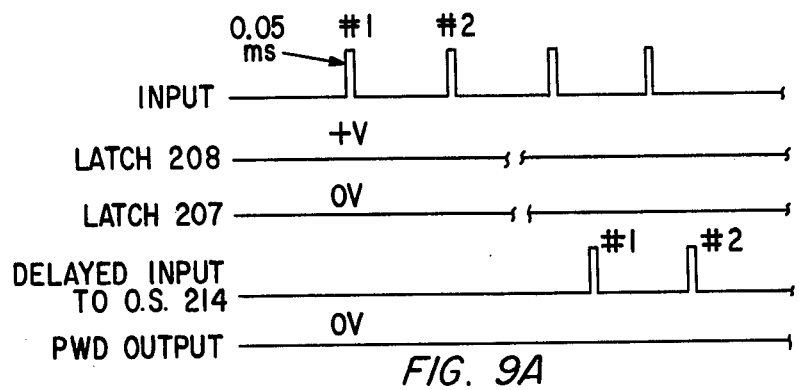
FIGS. 9A–9F are timing diagrams illustrating the operation of the circuitry of FIG. 8 for various pulse widths and repetition rates for the pacemaker pulses.

Reference is made to FIGS. 9A–9F for various combinations of input pacer pulse widths and repetition rates, in explanation of the operation of the circuitry of FIG. 8. FIG. 9A represents the case of an input pulse width smaller than 0.1 ms and a high repetition rate. In this case, the 20:1 counter 205 never reaches full frequency division and latch 207 (the 0.1 ms latch) never becomes set, and thus continually inhibits output Nand gate 215. Both latches 207 and 208 are repeatedly reset by one shot 214. The result is no PWD output. The duty cycle of the input pulse could be as high as 90%, as shown in FIG. 9a, but no PWD output will result.

Figure 9B:
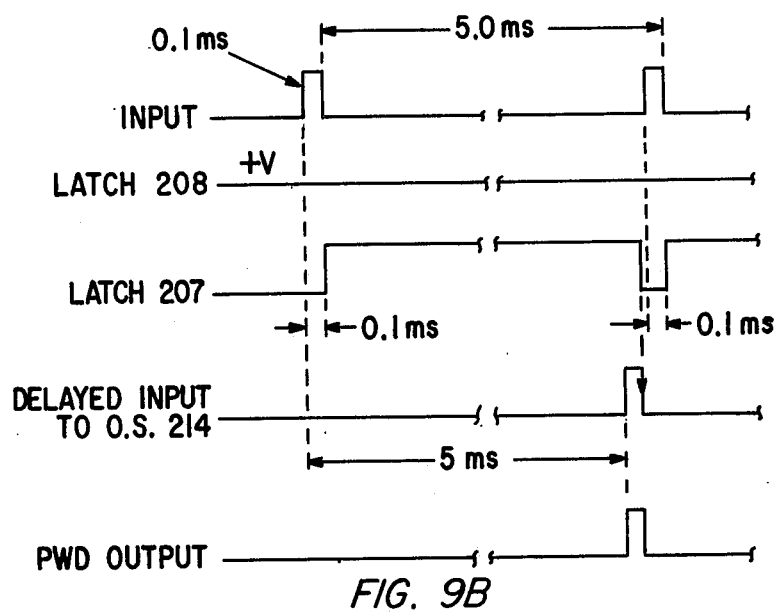
Figure 9C:
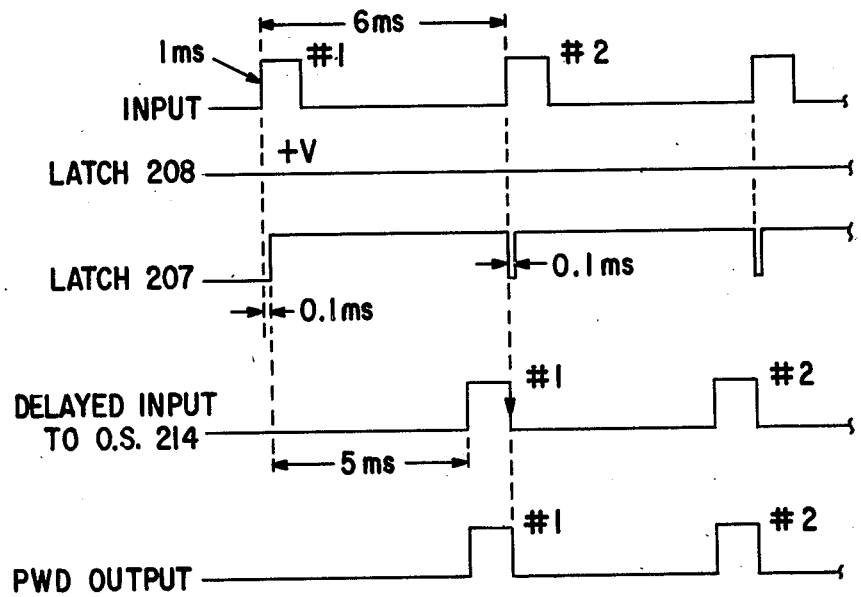
Figure 9D:
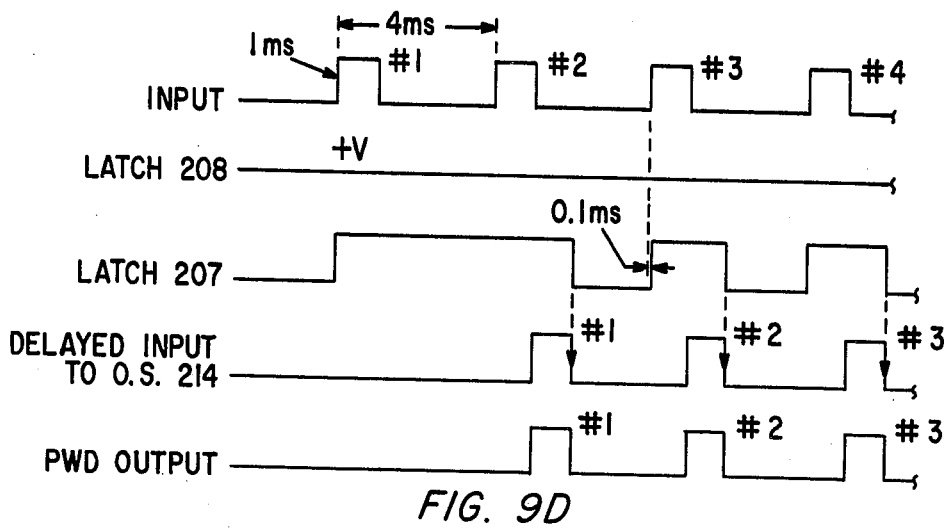

FIGS. 9B–9D represent the cases of an input pulse width within window limit, FIG. 9B having a 0.1 ms input pulse width, FIG. 9C having a 1 ms input pulse width, and FIG. 9D also having a 1 ms input pulse width with a smaller repetition rate then the fixed delay provided by shift register 209. In each of these cases, the 20:1 counter 205 reaches full frequency division and the 0.1 ms latch 207 is set 0.1 ms after the leading edge or the input pulse. Since the upper latch (5 ms latch) 208 never becomes set, the output Nand gate 215 is open for the delayed input pulse to pass in each case. FIG. 9B, for example, shows a 0.1 ms pulse just passing the PWD window of 0.1 ms–5 ms. FIG. 9C shows the same with a 1 ms input pulse of low repetition rate passing the PWD. FIG. 9D shows a 1 ms input pulse of higher repetition rate passing the PWD.

One duty cycle limiting factor is the lower limit of the PWD. In order to avoid ambiguity when pulse interval and fixed delay are exactly the same, one has only to inhibit the pulse input at input Nand gate 203 during the very short reset time of one shot 214. A reset time of 1–10 $\mu$s would have a negligible effect on the PWD operation, and high duty cycles can be achieved. Assuming a 0.8 ms pulse and a PWD of 0.1–5 ms window, a duty cycle of approximately 88% can be achieved. A lower PWD limit of 0.01 ms could result in a duty cycle of 99%.

Figure 9E:
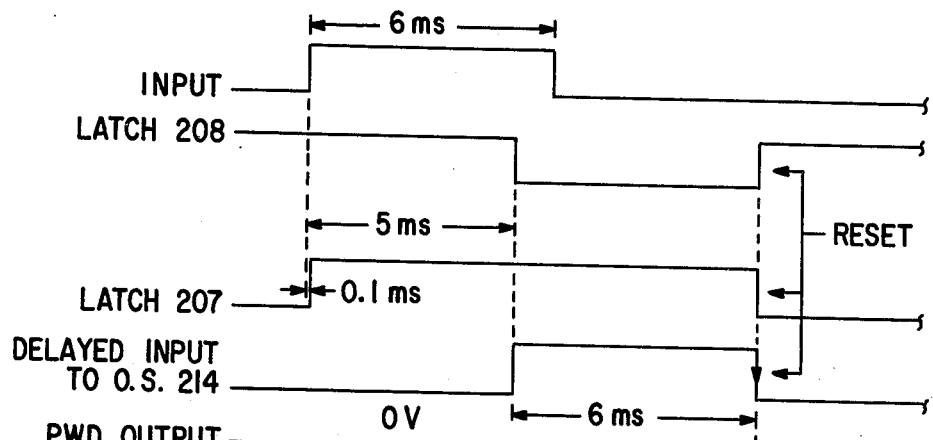
Figure 9F:
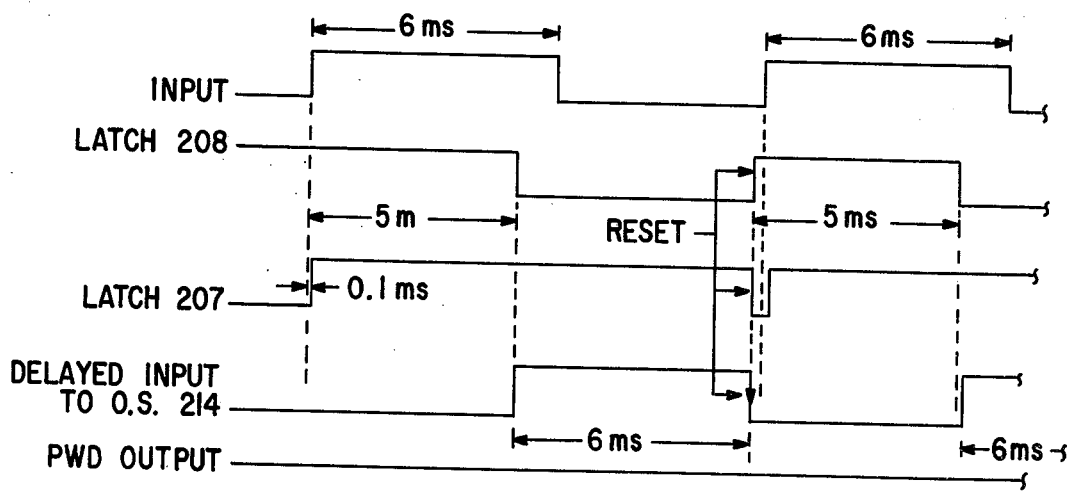

FIGS. 9E and 9F represent the cases of an input pulse width above window limits. In these cases, the 5 ms upper limit latch 208 inhibits output Nand gate 215 after 5 ms from the leading edge of the input pulse. The 0.1 ms lower-limit latch 207, of course, enables output gage 215, 0.1 ms after the leading edge of the input pulse.

Both latches 207 and 208 are reset by the trailing edge of the delayed pulse through one shot 214. With the Nand gate 215 inhibited the 6 ms input pulse cannot pass (see FIG. 9E). A 6 ms pulse of 11 ms interval and a PWD window of 0.1-5 ms would result in a duty cycle of 54%, but the PWD would not pass it (see FIG. 9F).

The duty cycle possible is proportional linearly to the input pulse width and inversely linearly proportional to the sum of the input pulse width and the lower PWD limit as shown on the equation below:

$$\text{duty cycle [\%]} = \frac{\text{(input pulse width (ms))}}{\text{(input pulse width + lower } PWD \text{ limit) (ms)}}$$

Duty cycles up to 99% can thus be achieved.

Figure 10:
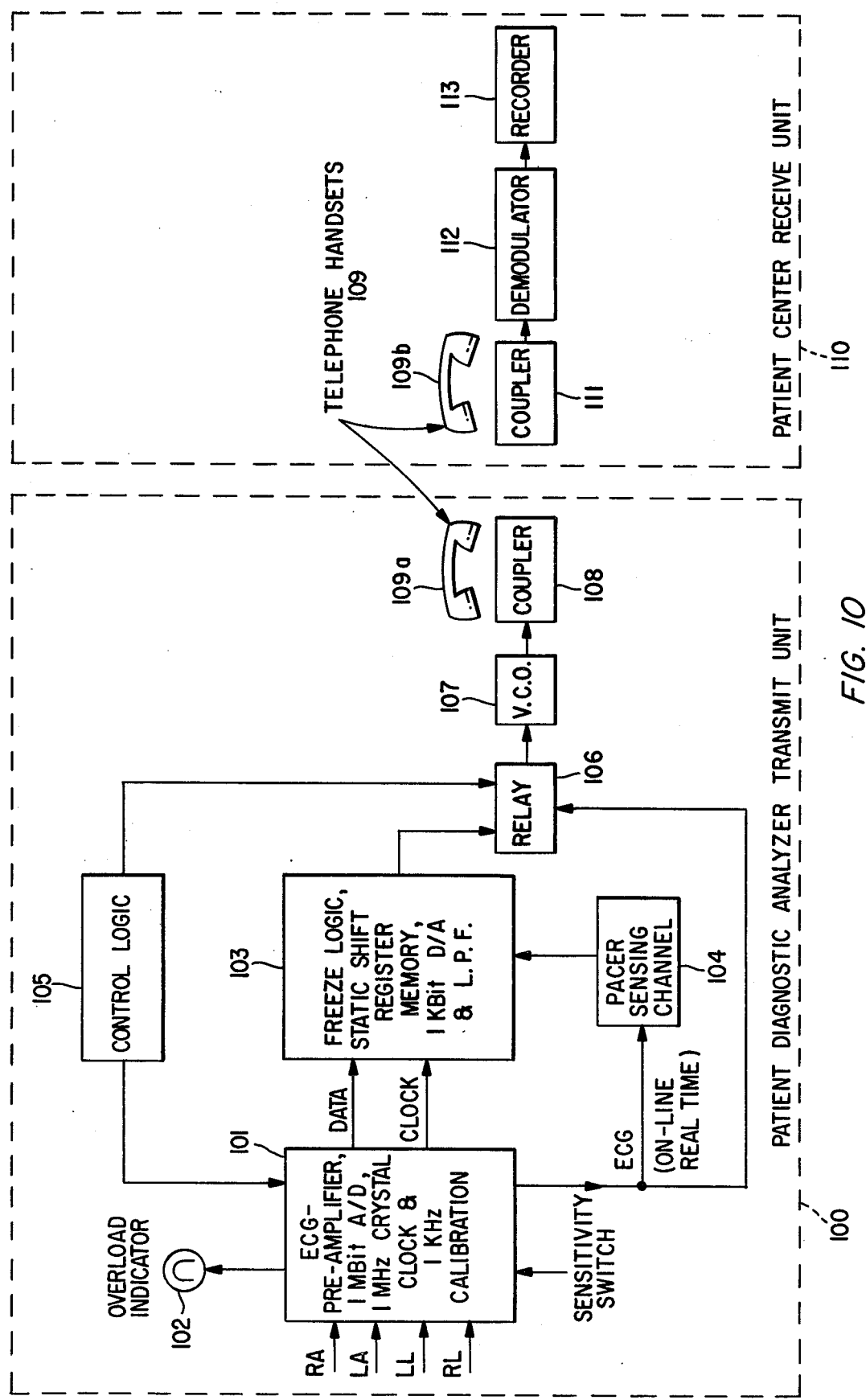
FIG. 10 is a block diagram of a telephone transmission system arrangement according to the invention.

FIG. 10 is a somewhat more detailed block diagram of the telephone system concept of the invention, in which there is provided a patient diagnostic analyzer transmit unit 100 and a patient center receive unit 110, remotely connected only via respective conventional telephone handsets present at the locations of the two units.

As seen in FIG. 10 the RA, LA, LL (and if needed due to an electrically noisy environment, RL) patient leads are coupled to the floating front end 101 of the transmit system, which, as before, feeds the data to the freeze logic etc. 103 and also to the pacer pulse sensing channel 104. The ECG input to channel 104 is also input to relay 106. Relay 106 and floating front end 101 are controlled by suitable control logic 105, as has been indicated hereinbefore with reference to block 67 of FIG. 3. FIG. 10 also includes the overload indicator 102 off of the floating front end and the clock being coupled to the freeze control circuitry 103, as well as the sensitivity switch input for controlling attenuation of the floating front end to ensure integrity of the pacer pulse.

The controlled output of relay 106 is coupled to a (FM subcarrier modulator) variable controlled oscillator (VCO) 107, the output (e.g a 2 KHz FM-modulator subcarrier) of which in turn is fed to a suitable audio coupling arrangement 108 for holding the handset 109a of a conventional telephone.

The signal transmitted over the telephone lines is received in another conventional telephone handset 109b via its audio coupler 111. The output of the latter is treated by a demodulator 112 which drives a recording device 113 such as a conventional strip chart recorder. Since the transmitting units sends a 2 KHz FM modulated subcarrier (in this example) through the telephone exchange(s) over existing telephone lines, the receiver side has only to demodulate the incoming FM subcarrier.

In case a digital readout of the pacer pulse width is desired, one could use the expanded analog waveform and arrive at an extremely accurate width measurement.

The patient diagnostic analyzer telephone system herein described transmits a lead I, II and III ECG configuration. Paced ECG is transmitted on-line and in real time. The 1 KHz 1Vpp squarewave is time-expanded X1000, transmitted, and received as an expanded 1 Hz analog signal in order to allow gain calibration at the receive side. The pacer pulse waveform is also time expanded X1000, transmitted, and received as an expanded analog signal, slow enough for any standard strip chart recorder. A hard strip copy of the true pacer pulse waveform is thus obtainable, and can be cleanly photocopied.

The patient diagnostic analyzer system contemplated by this invention, and in particular the telephone transmission arrangement, is capable of dealing with a relatively new parameter in pacemaker monitoring—the measurement of the decay time of the slope of the trailing edge of the pacer waveform. This new parameter is important in that the slope is proportional to the patient and wire resistance, and if the slope gets steeper, there is less resistance and therefore there may be more current drain and the battery will not last as long. This information is only available through providing an accurate reproduction of the actual pacer waveform. It is to be again emphasized, of course, that there is provided accurate information regarding the leading and trailing edges of the pacer pulse, and overshoots (if any). That is, in no way is the analog content changed; therefore the fidelity of the pacer waveform is maintained.

We claim:

1. In a system for evaluating a pacemaker operatively connected to a paced patient, the combination comprising:

electrically floating first means for converting an input signal containing artificially paced heart function information derived from the patient to a digital representation thereof of predetermined form and high rate, and second means connected to said first means for selectively deriving from said digital representation a reproduction in its true fidelity of at least one pacer pulse waveform generated by said pacemaker and present in said input signal, said second means comprising means for providing said reproduction magnified in time by a predetermined amount and including memory means for receiving said digital representation from said first means and means for controlling the movement of the digital information of said digital representation into and within the memory, said controlling means including means for selectively effecting recirculation of the memory content at a predetermined slower rate relative to the rate at which said digital information enters the memory.

2. A system according to claim 1 wherein said second means comprises third means connected to said controlling means and responsive to said input signal information for passing only those portions thereof pertaining to the pacer pulses.

3. A system according to claim 2 wherein said third means includes fourth means for converting said digital representation of said input signal information back to the original analog form thereof with high fidelity and fifth means connected to said controlling means for continuously searching said reconverted signal for pacer pulses and for eliminating from said reconverted analog signal all but said pacer pulses.

4. A system according to claim 3 wherein said fifth means includes foldover circuit means responsive to said reconverted analog signal for enabling processing of the pacer pulses regardless of the polarity thereof.

5. A system according to claim 3 wherein said fifth means includes threshold comparator means with pulse width discriminator means coupled to said threshold comparator means.

6. A system according to claim 3 further including means for recording the output of said fourth means.

7. A system according to claim 1 wherein said floating first means includes (a) seventh means for providing predetermined gain to said input signal;
(b) analog-to-digital converter means coupled to said seventh means for providing high bit rate, monobit, delta sigma modulation digitization of said input signal;
(c) clock means connected to said analog-to-digital converter means for providing at least one clock output of predetermined rate, said clock means thereby being synchronized with said analog-to-digital converter means; and
(d) electric isolation coupling means for coupling said digitized input signal and said clock output from said first means to the remainder of the system.

8. A system according to claim 7 wherein said second means includes recorder means and said first means further includes calibration signal injection means operatively coupled to said seventh means for providing an accurate time and amplitude validity check on virtually the entire system, and
eighth means for selectively controlling the amplitude of the input to said analog-to-digital converter means.

9. A system according to claim 1 wherein said second means includes recorder means, and further including a system internal calibration signal injection means for generating a calibration signal of constant pulse repetition rate and amplitude, said calibration signal being predeterminably magnified in time by said second means in the same manner as the pacer pulses, for enabling a validation of virtually the entire system and for permitting a proper recorder gain adjustment for recording said magnified pacer pulses.

10. A system according to claim 1 wherein said first means further includes overload detection and indication means for automatically providing an indication of said input signal to said first means being in excess of a predetermined threshold amplitude.

11. A system according to claim 10 wherein said indication means includes visual indication means and wherein an input exceeding the threshold automatically effects a visual indication of overload.

12. A system according to claim 10 wherein said overload detection and indication means includes means for automatically visually representing the pacemaker rate in an overload situation.

13. A system according to claim 1 further including means for recording the magnified reproduction of the pacer pulse and for providing a permanent copy thereof.

14. In a system for evaluating the cardiac function of a patient operatively connected to an artificial pacemaker pulse generating device, the combination comprising
electrically floating first means for converting an input signal from the patient containing artificially paced heart function information to a digital representation thereof of predetermined form;
second means for selectively deriving from said digital representation a portion thereof which is representative of an artificially generated pacer pulse present in said input signal from the patient, magnified in time by a predetermined amount;
third means for deriving said digitized output of said second means an analog waveform of said artificially generated pacer pulse in its true fidelity, magnified in time by said predetermined amount; and
fourth means for selectively providing as output of the system said magnified digitized representation of said selectively derived pacer pulse or said magnified analog waveform of said pacer pulse.

15. In a system for analysis of pacemaker devices operatively connected to patients, in which there is derived for evaluation from an input signal taken from a paced patient via standard ECG leads, pacer rate (interval), pacer pulse width and a high fidelity predeterminably magnified analog reproduction of selected ones of the pacer pulses generated by the patient's pacemaker device as well as a high fidelity on-line real time reproduction of the paced ECG of the patient, the combination comprising,
(a) first means for converting said input signal from the patient to a digital representation thereof of predetermined form;
(b) second means for deriving from the information contained in said input signal the individual pacer pulses generated by the patient's pacemaker device, in analog form of high fidelity;
(c) waveform magnification means responsive to said digital representation of said input signal from said first means and to said pacer pulses from said second means for selectively deriving from said digital representation a high fidelity analog reproduction of at least one pacer pulse originating from the patient's pacemaker and contained in said input signal, said pacer pulse analog reproduction being magnified in time a predetermined amount; and
(d) third means for selectively transmitting to a remote location or recording said magnified analog reproduction of said at least one pacer pulse.

16. In a system for evaluating a pacemaker device operatively connected to a paced patient, the combination which comprises
(a) first means for deriving from the paced patient an input signal containing heart function information including pacer pulses artificially generated by the patient's pacemaker device;
(b) second means for converting said input signal into a digital representation thereof of predetermined monobit form,
(c) monobit multi-element memory means;
(d) third means for controlling the flow of digital information from said second means to said memory means;
(e) clock means synchronized with said second means and operatively coupled to said memory means for effecting and controlling circulation of said digital information from element to element through said memory means at a first predetermined rate;
(f) fourth means for effecting recirculation of a selected portion of said digital information through said memory means for a predetermined time and simultaneously causing said third means to inhibit the input of any further information to the memory means during the period of information recirculation; and
(g) fifth means for effecting a synchronous change in the rate of recirculation of said digital information in said memory means from said first predetermined rate to a second predetermined rate while maintaining intact all recirculating information, thereby effecting as output from said memory said recirculating information predeterminably magnified in time in accordance with said change in recirculation rate.

17. In a system for providing transtelephonic information derived from a patient remotely located from an information processing center, in which the information to be transmitted to the center is related to heart function and includes pacemaker device-generated pulse information, the combination comprising:
  (a) electrically isolated first means local to the patient and responsive to the input of said information for providing a high rate, monobit digitization of said information; and
  (b) second means responsive to and separate from said first means for selectively isolating from said digitized representation of said information a portion thereof pertaining to at least one pacemaker device-generated pulse and for providing same in a form constituting a reproduction of the pacer pulse waveform in its true fidelity and magnified a predetermined amount in time for transmission to the information processing center.

18. In a system according to claim 11 wherein said second means includes multi-element memory means, third means for controlling the flow of said digitized input signal information to said memory means, fourth means for controlling the movement of said digital information at a first predetermined rate in the circulation thereof through the elements of said memory means, fifth means for selectively effecting recirculation of said information in said memory means for a predetermined time and simultaneously causing said third means to inhibit the input of any further information into said memory means during the information recirculation time, and sixth means for synchronously effecting a change in the rate of recirculation of said information in said memory means from said first predetermined rate to a second predetermined rate while maintaining intact and recirculating the information in said memory means.

19. In a system for evaluating a pacemaker operatively connected to a patient, the combination comprising
  electrically floating first means for converting an input signal containing artificially paced heart function information derived from the patient to a digital representation thereof of predetermined form and high rate, said first means including means for providing predetermined gain to said input signal, analog-to-digital converter means operatively coupled to said predetermined gain means, second means for selectively controlling the amplitude of the input to said analog-to-digital converter means, and calibration signal injection means operatively coupled to said predetermined gain means for providing upon actuation an accurate time and amplitude validity check on virtually the entire system, said second means including reciprocal attenuation network means operatively coupled to said predetermined gain means and to said calibration signal injection means for providing selective attenuation of the predetermined gain provided by said predetermined gain means and reciprocal attenuation with regard to the calibration signal provided by said calibration signal injection means in order to effect at the input to said analog-to-digital converter said calibration signal with constant amplitude regardless of the attenuation setting selected for said attenuation network means,
  and third means connected to said first means for selectively deriving from said digital representation a reproduction in its true fidelity of at least one calibration pulse or at least one pacer pulse waveform generated by said pacemaker, said third means including means for providing said reproduction magnified in time by a predetermined amount.

20. A system according to claim 19 wherein the output of said predetermined gain means is directly connected to an input to said analog-to-digital converter means and wherein said first means further includes overload detection and indication means connected to the input connection of said predetermined means to said A/D converter means for automatically providing an indication of said input signal to said first means being in excess of a predetermined threshold amplitude.

21. A system according to claim 20 wherein said overload detection and indication means includes fourth means for providing a blinking visual indication of amplitude overload, the frequency of which blinking is at the rate of the pacer pulses appearing in the input signal to said first means.

22. In a system for evaluating a pacemaker operatively connected to a paced patient, the combination comprising
  electrically floating first means for converting an input signal containing artificially paced heart function information derived from the patient to a digital representation thereof of predetermined form and high rate,
  and second means connected to said first means for selectively deriving from said digital representation a reproduction in its true fidelity of at least one pacer pulse waveform generated by said pacemaker and present in said input signal, said reproduction being magnified in time by a predetermined amount, said second means including multi-element memory means having an output, third means for controlling the flow of said digitized input signal information to said memory means, fourth means for controlling the movement of said digital information at a first predetermined rate in the circulation thereof through said memory means, fifth means for selectively effecting recirculation of said information in said memory means for a predetermined time and simultaneously causing said third means to inhibit the input of any further information into said memory means during the information recirculation time, and sixth means for synchronously effecting a change in the rate of circulation of said information in said memory means from said first predetermined rate to a second predetermined rate while maintaining intact and recirculating the information in said memory means.

23. A system according to claim 22 wherein said third means includes clock means for selectively providing a plurality of different rates of information recirculation in said memory means, and said sixth means includes first logic means operatively coupled to said clock means and to said memory means for enabling said synchronous change in the rate of recirculation of the information in said memory means by controllably effecting a synchronous switching of said clock from providing a clock signal having a first predetermined rate to providing a clock signal having a second predetermined rate.

24. A system according to claim 23 wherein said second means further includes seventh means responsive to said input signal information for passing only those portions thereof pertaining to the artificially generated pacer pulses and second logic means coupled to said seventh means and to said fourth means for enabling a recirculation of the information in said memory means and a switching of the recirculation rate thereof only when there is present at the output of said seventh means an artificially generated pacer pulse derived from said input signal.

25. In a system for providing transtelephonic information derived from a patient remotely located from an information processing center, in which the information to be transmitted to the center is related to heart function and includes pacemaker device-generated pulse information, which system includes transmission means, receiving means and hard copy recording means, the combination comprising:

(a) electrically isolated first means local to the patient and responsive to the input of said information for providing a high rate, monobit digitization of said information; and (b) second means responsive to and separate from said first means for selectively isolating from said digitized representation of said information a portion thereof pertaining to at least one pacemaker device-generated pulse and for providing same in form constituting a reproduction of the pacer pulse waveform in its true fidelity and magnified a predetermined amount in time for transmission to the information processing center, wherein said first means includes calibration means selectively providing in place of said information a high rate, monobit digitization of a clock waveform of preestablished pulse repetition rate and amplitude, for enabling a validity check of virtually the entire system, and wherein said second means includes means for converting said digitized calibration output of said first means to analog form of high fidelity relative to the original clock waveform and magnified said predetermined amount in time for transmission as a calibration signal to the center, and further including means at the receive side of the transtelephonic infomation communication for enabling proper receiver gain adjustment based on said transmitted calibration signal and thereby enabling an accurate hard copy reproduction of the original waveform of said information selected for transmission in its true fidelity.

26. In a system according to claim 25 further including means for selecting for transmission either of: (1) said heart function information containing artificially generated pacer pulses in virtually its original form, (2) said at least one isolated and magnified pacer pulse, and (3) said magnified calibration signal.

* * * * *